US011755111B2

(12) United States Patent
Nickerson

(10) Patent No.: US 11,755,111 B2
(45) Date of Patent: Sep. 12, 2023

(54) SPATIALLY AWARE COMPUTING HUB AND ENVIRONMENT

(71) Applicant: ARKH, Inc., Dallas, TX (US)

(72) Inventor: Landon Nickerson, Dallas, TX (US)

(73) Assignee: ARKH, Inc., Dallas, TX (US)

( * ) Notice: Subject to any disclaimer, the term of this patent is extended or adjusted under 35 U.S.C. 154(b) by 0 days.

(21) Appl. No.: 17/203,654

(22) Filed: Mar. 16, 2021

(65) Prior Publication Data
US 2021/0286433 A1  Sep. 16, 2021

Related U.S. Application Data

(60) Provisional application No. 63/083,864, filed on Sep. 26, 2020, provisional application No. 62/990,059, filed on Mar. 16, 2020.

(51) Int. Cl.
*G06F 3/01* (2006.01)
*G06F 3/038* (2013.01)
(Continued)

(52) U.S. Cl.
CPC ............ *G06F 3/016* (2013.01); *G06F 3/038* (2013.01); *G06Q 20/3224* (2013.01);
(Continued)

(58) Field of Classification Search
CPC .. G06F 3/016; G06F 3/038; G06F 2203/0331; G06Q 20/3224; G06Q 20/321;
(Continued)

(56) References Cited

U.S. PATENT DOCUMENTS

| 5,945,978 A | 8/1999 | Holmes |
| 7,215,321 B2 | 5/2007 | SanGiovanni |
(Continued)

FOREIGN PATENT DOCUMENTS

| WO | 2019229698 A1 | 12/2019 |
| WO | 2020170105 A1 | 8/2020 |

OTHER PUBLICATIONS

Amazon; "Introducing Echo Loop—Keep Alexa on Hand"; https://web.archive.org/web/20200310162907/https://www.amazon.com/Echol-Loop/dp/B07K57PBKT; Mar. 10, 2020; 6 pages.
(Continued)

*Primary Examiner* — Ariel A Balaoing
(74) *Attorney, Agent, or Firm* — Conley Rose, P.C.; Grant Rodolph; Robert E. Kent

(57) ABSTRACT

Aspects of the disclosure provide for a sensory augmentation system. In some examples, the sensory augmentation system includes a first electro-tactile stimulator comprising at least one user interaction element driven by a driver and contactable to a human body to provide stimulation having a first stimulation waveform and a signal generation and sensing processor configured to receive data corresponding to information to be communicated to the user. The signal generation and sensing processor may generate a first instruction to the driver, the first instruction corresponding to the first stimulation waveform. The driver may generate the stimulation having the first stimulation waveform in response to the first instruction.

18 Claims, 16 Drawing Sheets

(51) Int. Cl.
*G06Q 30/0601* (2023.01)
*G06Q 20/32* (2012.01)
*G09B 9/00* (2006.01)
*G06Q 20/36* (2012.01)
*G16H 40/67* (2018.01)
*G06N 20/00* (2019.01)

(52) U.S. Cl.
CPC . *G06Q 30/0639* (2013.01); *G06F 2203/0331* (2013.01); *G06N 20/00* (2019.01); *G06Q 20/321* (2020.05); *G06Q 20/36* (2013.01); *G09B 9/00* (2013.01); *G16H 40/67* (2018.01)

(58) Field of Classification Search
CPC .... G06Q 20/36; G06Q 30/0639; G16H 40/67; G06N 20/00; G09B 9/00
See application file for complete search history.

(56) References Cited

U.S. PATENT DOCUMENTS

| | | |
|---|---|---|
| 7,512,185 B2 | 3/2009 | Sharon et al. |
| 7,706,404 B2 | 4/2010 | Fleming |
| 7,716,586 B2 | 5/2010 | Dieberger et al. |
| 7,756,002 B2 | 7/2010 | Batra et al. |
| 8,031,172 B2 | 10/2011 | Kruse et al. |
| 8,232,976 B2 | 7/2012 | Yun et al. |
| 8,378,795 B2 | 2/2013 | Steger et al. |
| 8,599,152 B1 | 12/2013 | Wurtenberger et al. |
| 8,698,764 B1 | 4/2014 | Karakotsios et al. |
| 8,799,803 B2 | 8/2014 | Amm |
| 8,809,716 B2 | 8/2014 | Gohng et al. |
| 8,830,163 B2 | 9/2014 | Sim et al. |
| 8,860,763 B2 | 10/2014 | Privault et al. |
| 9,030,424 B2 | 5/2015 | Shih et al. |
| 9,141,148 B2 | 9/2015 | Richter et al. |
| 9,141,272 B1 | 9/2015 | Cleron et al. |
| 9,229,540 B2 | 1/2016 | Mandella et al. |
| 9,268,483 B2 | 2/2016 | Dennis et al. |
| 9,330,545 B2 | 5/2016 | Kempin et al. |
| 9,335,790 B2 | 5/2016 | Stotler |
| 9,335,823 B2 | 5/2016 | Modarres et al. |
| 9,383,839 B1 | 7/2016 | Rost et al. |
| 9,412,002 B2 | 8/2016 | Magi |
| 9,446,665 B2 | 9/2016 | Abel et al. |
| 9,474,580 B2 | 10/2016 | Hannaford et al. |
| 9,535,550 B2 | 1/2017 | Levesque et al. |
| 9,535,557 B2 | 1/2017 | Bernstein et al. |
| 9,547,366 B2 | 1/2017 | Ullrich et al. |
| 9,600,076 B2 | 3/2017 | Levesque et al. |
| 9,600,083 B2 | 3/2017 | Levesque et al. |
| 9,606,624 B2 | 3/2017 | Cruz-Hernandez et al. |
| 9,645,647 B2 | 5/2017 | Levesque |
| 9,690,377 B2 | 6/2017 | Lee et al. |
| 9,690,381 B2 | 6/2017 | Levesque et al. |
| 9,690,382 B1 | 6/2017 | Moussette et al. |
| 9,696,822 B2 | 7/2017 | Dow et al. |
| 9,713,500 B2 | 7/2017 | Kim et al. |
| 9,746,921 B2 | 8/2017 | Mallinson |
| 9,746,933 B2 | 8/2017 | Burba et al. |
| 9,778,813 B2 | 10/2017 | Shenfield et al. |
| 9,785,123 B2 | 10/2017 | Mansour et al. |
| 9,792,272 B2 | 10/2017 | Hicks |
| 9,798,388 B1 | 10/2017 | Murali |
| 9,813,841 B2 | 11/2017 | Yin et al. |
| 9,830,782 B2 | 11/2017 | Morrell et al. |
| 9,880,697 B2 | 1/2018 | Anderson et al. |
| 9,891,709 B2 | 2/2018 | Heubel |
| 9,904,409 B2 | 2/2018 | Lee et al. |
| 9,927,902 B2 | 3/2018 | Burr et al. |
| 9,939,963 B2 | 4/2018 | Beckman |
| 9,945,818 B2 | 4/2018 | Ganti et al. |
| 9,946,505 B2 | 4/2018 | Becze et al. |
| 9,965,033 B2 | 5/2018 | Park et al. |
| 10,007,772 B2 | 6/2018 | Slaby et al. |
| 10,061,458 B1 | 8/2018 | Bristol et al. |
| 10,065,114 B2 | 9/2018 | Goetgeluk et al. |
| 10,075,814 B2 | 9/2018 | Sydir et al. |
| 10,088,902 B2 | 10/2018 | Keller et al. |
| 10,126,779 B2 | 11/2018 | von Badinski et al. |
| 10,126,941 B2 | 11/2018 | Zhu et al. |
| 10,146,308 B2 | 12/2018 | Cruz-Hernandez et al. |
| 10,171,129 B1 | 1/2019 | Hammerschmidt et al. |
| 10,183,217 B2 | 1/2019 | Chen et al. |
| 10,185,670 B2 | 1/2019 | Litichever et al. |
| 10,216,272 B2 | 2/2019 | Keller et al. |
| 10,285,013 B2 | 5/2019 | Ledvina et al. |
| 10,331,777 B2 | 6/2019 | Hicks et al. |
| 10,346,038 B2 | 7/2019 | England et al. |
| 10,372,221 B2 | 8/2019 | Robert et al. |
| 10,372,270 B2 | 8/2019 | Hoggarth et al. |
| 10,386,960 B1 | 8/2019 | Smith |
| 10,416,774 B2 | 9/2019 | Weddle et al. |
| 10,437,337 B2 | 10/2019 | Park |
| 10,444,834 B2 | 10/2019 | Vescovi et al. |
| 10,490,035 B2 | 11/2019 | Morrell et al. |
| 10,496,193 B1 | 12/2019 | Alfano et al. |
| 10,496,235 B2 | 12/2019 | Woley et al. |
| 10,503,454 B2 | 12/2019 | Sirpal et al. |
| 10,509,469 B2 | 12/2019 | Erivantcev et al. |
| 10,514,780 B2 | 12/2019 | Su et al. |
| 10,514,831 B2 | 12/2019 | Sirpal et al. |
| 10,514,877 B2 | 12/2019 | Becze |
| 10,528,230 B2 | 1/2020 | Sirpal et al. |
| 10,528,312 B2 | 1/2020 | Reeves |
| 10,534,447 B2 | 1/2020 | Li |
| 10,540,052 B2 | 1/2020 | Gimpl et al. |
| 10,540,087 B2 | 1/2020 | Sirpal et al. |
| 10,545,580 B2 | 1/2020 | Yang et al. |
| 10,545,712 B2 | 1/2020 | Reeves et al. |
| 10,547,716 B2 | 1/2020 | Jeon et al. |
| D875,097 S | 2/2020 | Martin et al. |
| 10,552,007 B2 | 2/2020 | Sirpal et al. |
| 10,558,321 B2 | 2/2020 | Sirpal et al. |
| 10,558,414 B2 | 2/2020 | Reeves et al. |
| 10,558,415 B2 | 2/2020 | de Paz |
| 10,572,095 B2 | 2/2020 | Sirpal et al. |
| 10,579,099 B2 | 3/2020 | Wang et al. |
| 10,592,061 B2 | 3/2020 | Sirpal et al. |
| 10,599,218 B2 | 3/2020 | Saboune et al. |
| 10,602,556 B2 | 3/2020 | Foster et al. |
| 10,606,359 B2 | 3/2020 | Levesque et al. |
| D880,487 S | 4/2020 | Martin et al. |
| 10,627,902 B2 | 4/2020 | Vescovi et al. |
| 10,652,383 B2 | 5/2020 | Selim |
| 10,664,121 B2 | 5/2020 | Sirpal et al. |
| 10,664,129 B2 | 5/2020 | Lee et al. |
| 10,678,411 B2 | 6/2020 | Reeves et al. |
| 10,684,478 B2 | 6/2020 | Osterhout |
| 10,698,486 B2 | 6/2020 | Reynolds et al. |
| 10,705,674 B2 | 7/2020 | Gimpl et al. |
| 10,706,251 B2 | 7/2020 | Shim et al. |
| 10,713,907 B2 | 7/2020 | Anderson et al. |
| 10,716,371 B2 | 7/2020 | Ward |
| 10,719,191 B2 | 7/2020 | Sirpal et al. |
| 10,719,232 B2 | 7/2020 | Tse |
| 10,739,142 B2 | 8/2020 | Meier et al. |
| 10,740,058 B2 | 8/2020 | Sirpal et al. |
| 10,768,747 B2 | 9/2020 | Wang et al. |
| 10,775,891 B2 | 9/2020 | Sinclair et al. |
| 10,795,448 B2 | 10/2020 | Miller |
| 10,803,281 B2 | 10/2020 | Han et al. |
| 10,831,358 B2 | 11/2020 | Webber |
| 10,845,938 B2 | 11/2020 | Sirpal et al. |
| 10,849,519 B2 | 12/2020 | Mendenhall et al. |
| 10,852,154 B1 | 12/2020 | Knas et al. |
| 10,852,700 B2 | 12/2020 | Abramov |
| 10,853,013 B2 | 12/2020 | Sirpal et al. |
| 10,853,016 B2 | 12/2020 | Sirpal et al. |
| 10,871,871 B2 | 12/2020 | Cassar et al. |
| 10,893,833 B2 | 1/2021 | Harverinen et al. |
| 10,915,214 B2 | 2/2021 | Sirpal et al. |
| 10,922,870 B2 | 2/2021 | Vaganov |
| 10,942,615 B2 | 3/2021 | Helmes et al. |

(56) References Cited

U.S. PATENT DOCUMENTS

| | | | |
|---|---|---|---|
| 10,949,051 B2 | 3/2021 | Sirpal et al. | |
| 10,955,974 B2 | 3/2021 | Griffin | |
| 10,963,007 B2 | 3/2021 | de Paz et al. | |
| 10,964,178 B2 | 3/2021 | Aleksov et al. | |
| 10,976,820 B2 | 4/2021 | Ganadas et al. | |
| 10,976,822 B2 | 4/2021 | Dogiamis et al. | |
| 10,983,559 B2 | 4/2021 | Reeves et al. | |
| 10,990,242 B2 | 4/2021 | Sirpal et al. | |
| 11,010,047 B2 | 5/2021 | Sirpal et al. | |
| 11,061,476 B2 | 7/2021 | Remaley et al. | |
| 11,073,826 B2 | 7/2021 | Celia et al. | |
| 11,093,200 B2 | 8/2021 | Reeves et al. | |
| 11,093,769 B2 | 8/2021 | Dow et al. | |
| 11,106,355 B2 | 8/2021 | Kolondra et al. | |
| 11,119,633 B2 | 9/2021 | Yamamoto | |
| 11,132,161 B2 | 9/2021 | de Paz | |
| 11,137,796 B2 | 10/2021 | Sirpal et al. | |
| 11,151,234 B2 | 10/2021 | Kontsevich et al. | |
| 11,182,046 B2 | 11/2021 | Sirpal et al. | |
| 11,221,646 B2 | 1/2022 | Sirpal et al. | |
| 11,221,647 B2 | 1/2022 | Sirpal et al. | |
| 11,221,649 B2 | 1/2022 | Sirpal et al. | |
| 11,226,710 B2 | 1/2022 | Sirpal et al. | |
| 11,231,786 B1 | 1/2022 | Elangovan | |
| 11,243,521 B2 | 2/2022 | Celia et al. | |
| 11,262,792 B2 | 3/2022 | de Paz et al. | |
| 2014/0143737 A1 | 5/2014 | Mistry et al. | |
| 2015/0277559 A1* | 10/2015 | Vescovi | G06F 3/017 345/173 |
| 2015/0338916 A1 | 11/2015 | Priyantha et al. | |
| 2016/0054800 A1* | 2/2016 | Kim | G06F 3/017 345/156 |
| 2016/0077587 A1 | 3/2016 | Kienzle et al. | |
| 2016/0292563 A1* | 10/2016 | Park | G06F 3/016 |
| 2016/0357258 A1* | 12/2016 | Yeom | G06F 3/011 |
| 2017/0200353 A1* | 7/2017 | Brown | G08B 6/00 |
| 2018/0066945 A1 | 3/2018 | Meier et al. | |
| 2018/0136729 A1* | 5/2018 | Kim | G06F 3/0346 |
| 2018/0349699 A1 | 12/2018 | O'Connell et al. | |
| 2019/0007093 A1 | 1/2019 | Hammerschmidt et al. | |
| 2019/0039570 A1 | 2/2019 | Foster et al. | |
| 2019/0135229 A1 | 5/2019 | Ledvina et al. | |
| 2019/0155385 A1 | 5/2019 | Lim et al. | |
| 2019/0199398 A1 | 6/2019 | Hammerschmidt et al. | |
| 2019/0272427 A1* | 9/2019 | Yin | G10L 15/22 |
| 2019/0273636 A1 | 9/2019 | Batra et al. | |
| 2019/0317177 A1 | 10/2019 | Ertan et al. | |
| 2019/0332140 A1* | 10/2019 | Wang | G06F 3/011 |
| 2020/0014526 A1 | 1/2020 | Hammerschmidt et al. | |
| 2020/0053689 A1 | 2/2020 | McQueen et al. | |
| 2020/0106877 A1 | 4/2020 | Ledvina et al. | |
| 2020/0241641 A1* | 7/2020 | Vescovi | G06F 21/31 |
| 2020/0272221 A1 | 8/2020 | Foster et al. | |
| 2020/0275369 A1 | 8/2020 | Foster et al. | |
| 2020/0280952 A1 | 9/2020 | Sasoglu et al. | |
| 2020/0387222 A1* | 12/2020 | Adesanya | G06F 3/0383 |
| 2021/0064132 A1* | 3/2021 | Rubin | G06F 3/017 |
| 2021/0089126 A1 | 3/2021 | Nickerson | |

OTHER PUBLICATIONS

Kickstarter; "Circular Smart Ring—Sleep, Energy, Performance. Evolved."; http://web.archive.org/web/20200202025937/https://www.kickstarter.com/projects/circular-ring/cirulartm-smart-ring-sleep-energy-performance-evolved; Feb. 2, 2020; 3 pages.

Jakcom; "Jakcom R3 Instruction"; https://web.archive.org/web/20190903144307/http://www.jakcom.com/ins/R3/JAKCOM_R3.html; Sep. 3, 2019; 4 pages.

McLear; "McLear Ring"; https://web.archive.org/web/20190820205244/https://mclear.com/product/payment-ring/; Aug. 20, 2019; 7 pages.

NFC; "NFC Ring—Safe, Simple, Secure. One Smart Ring, Unlimited Possibilities"; https://web.archive.org/web/20190806195338/https://nfcring.com/; Aug. 6, 2019; 3 pages.

Orii; "Product Details"; https://web.archive.org/web/20190728004048/https://orii.io/products/orii; Jul. 28, 2019; 6 pages.

Oura; "Understand Your Body with Oura Ring & Improve Your Health"; https://web.archive.org/web/20191019192847/https://ouraring.com/why-oura/; Oct. 19, 2019; 6 pages.

Sleepon; "Go2Sleep (HST)"; https://www.sleepon.us/go2sleep/; Nov. 27, 2019; 10 pages.

Purcher, Jack; "Apple Won 59 Patents Today Covering Augmented Reality 3D Reconstruction and More"; Patently Apple; Oct. 15, 2019; 6 pages.

Roemmele, Brian; "What is the New Apple U1 Chip, and Why is it Important?"; Quora; Sep. 13, 2019; 17 pages.

Techcrunch; "Lego Sets Its Eye on the Future with Apple ARKit 2"; YouTube; Jun. 4, 2018; 1 page.

Han, Teng, et al.; "Frictio: Passive Kinesthetic Force Feedback for Smart Ring Output"; UIST; Oct. 22-25, 2017 Quebec City, Canada; 12 pages.

PCT International Search Report and PCT Written Opinion of the International Searching Authority; PCT/2020/044435; dated Nov. 24, 2020; 16 pages.

Office Action dated Mar. 16, 2022; U.S. Appl. No. 16/944,506, filed Jul. 31, 2020; 24 pages.

Office Action dated Dec. 8, 2021; U.S. Appl. No. 16/944,506, filed Jul. 31, 2020; 5 pages.

Final Office Action dated Jul. 6, 2022; U.S. Appl. No. 16/944,506, filed Jul. 31, 2020; 32 pages.

Advisory Action dated Oct. 17, 2022; U.S. Appl. No. 16/944,506, filed Jul. 31, 2020; 5 pages.

Nickerson, Landon; U.S. Appl. No. 18/168,979, filed Feb. 14, 2023; Title: Spatially Aware Computing Hub Environment; 75 pages.

* cited by examiner

SPATIALLY AWARE COMPUTING HUB AND ENVIRONMENT

CROSS REFERENCE TO RELATED APPLICATIONS

This application claims priority to U.S. Provisional Patent Application No. 62/990,059, filed on Mar. 16, 2020 and titled "System and Method for Sensory Augmentation" and U.S. Provisional Patent Application No. 63/083,864, filed on Sep. 26, 2020 and titled "Spatially Aware Computing Hub and Environment," each of which is hereby incorporated herein by reference in its entirety.

BACKGROUND

The statements in this section merely provide background information related to the present disclosure and may not constitute prior art. Frequently, humans desire to communicate with others at a distance or with machines. However, typical sensory data provided to a human by a machine-human interface occupies one of the five senses, especially hearing or sight, rendering that sense distracted from other inputs. Moreover, individuals with disabilities such as hearing loss or vision impairment have difficulty interacting with such machine-human interfaces. Existing machine-human interfaces are often unsuited for high distraction environments, environments necessitating silences, or environments where a user must actively monitor real-world surroundings rather than an electronic device. Thus, there is a need for systems and methods as discussed herein.

SUMMARY

Aspects of the disclosure provide for a sensory augmentation system. In some examples, the sensory augmentation system includes a first electro-tactile stimulator comprising at least one user interaction element driven by a driver and contactable to a human body to provide stimulation having a first stimulation waveform and a signal generation and sensing processor configured to receive data corresponding to information to be communicated to the user. The signal generation and sensing processor may generate a first instruction to the driver, the first instruction corresponding to the first stimulation waveform. The driver may generate the stimulation having the first stimulation waveform in response to the first instruction.

Other aspects of the disclosure provide for a method of sensory augmentation. In at least some examples, the method includes providing, by a computing device, a wireless transmission corresponding to text, receiving, by a first electro-tactile stimulator, the wireless transmission, generating, by a signal generation and sensing processor of the first electro-tactile stimulator, a first instruction to an electrode driver, the first instruction corresponding to a first stimulation waveform representing the text, generating, by the electrode driver, the first stimulation waveform in response to the first instruction, and providing, by an electrode array driven by the electrode driver, electrical stimulation to a human body, the electrical stimulation corresponding to the text.

Other aspects of the disclosure provide for a sensory augmentation system. In at least some examples, the sensory augmentation system includes a hub comprising a processor and memory. The hub configured to store data regarding a context environment, determine and maintain an indication of a relative position of multiple items in the context environment, determine and maintain a relative position of a computing device in the context environment, and based on the determined relative positions of the multiple items and the computing device, determine an interaction has occurred between a user of the computing device and one of the multiple items.

BRIEF DESCRIPTION OF THE DRAWINGS

For a more complete understanding of this disclosure, reference is now made to the following brief description, taken in connection with the accompanying drawings and detailed description, wherein like block numerals represent like parts.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The human body contains a variety of different nerves. Many such nerves are capable of detecting mechanical or electrical stimulus. Moreover, it has been determined that many such nerves can be electrically stimulated to induce sensations, including sensations of mechanical stimuli. As such, one may appreciate that an electrical stimulus may communicate information via excitation of nerves.

Figure 1:
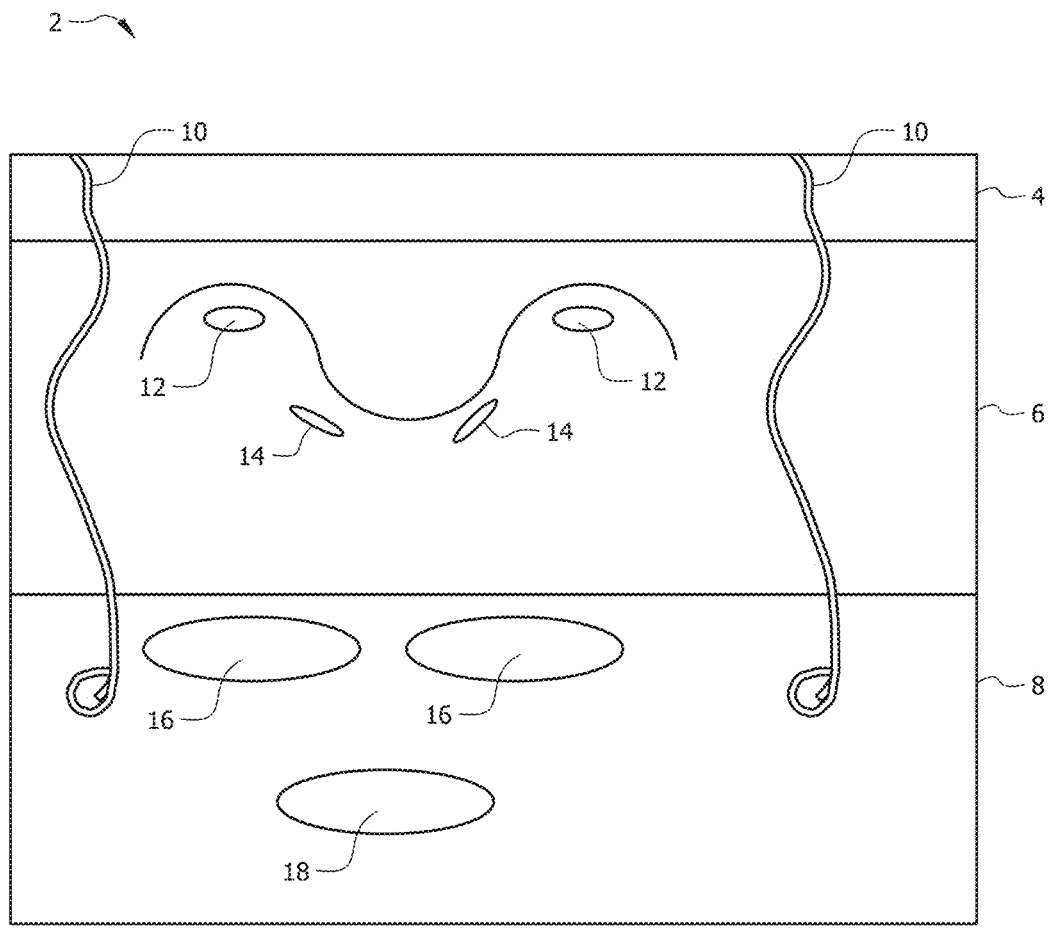
FIG. 1 is an example depiction of layers of skin and human nerves in accordance with aspects of the disclosure.

The various nerves may be classified or categorized. For example, different stimuli may be perceived by different nerves. By stimulating the different nerves, different sensations may be evoked. Moreover, different nerves perceive stimuli in different spatial relation, thus different nerves may be stimulated as well, to communicate differing messages. For instance, with reference to FIG. 1, four example types of nerves are disclosed. The human skin may have a stratum corneum 4 overlaying the epidermis 6. Various nerves are present in the epidermis 6. Moreover, the epidermis 6 may overlay the dermis 8. Various nerves may also be located in the dermis 8. For context, two sweat ducts 10 are shown as well.

Among the nerves, a Meissner corpuscle 12, a Merkel cell 14, a Ruffini ending 16, and a Pacinian corpuscle 18 are shown. In various instances, the Merkel cell 14 is activated by static pressure. In various instances, the Meissner corpuscle 12 is activated by time-varying vibrations, as is the Pacinian corpuscle 18. In various instances, one may appreciate that the Ruffini ending 16 and the Pacinian corpuscle 18 may have different resonant frequencies. For instance, the Ruffini ending 16 may resonate at 30 Hz and the Pacinian corpuscle 18 at 250 Hz. Moreover, myelinated nerves may comprise insulated nerves covered by a myelin sheath with gaps spaced at Nodes of Ranvier.

The different properties of the different nerves aspects may be exploited by different types of electrical stimulation, such that stimulation having both time variant, mode variant (e.g., the type of nerves activated), location variant, intensity variant, and sequence variant, and/or other path variant characteristics can communicate a limitless character set and immense amounts of human-readable information. Thus, by stimulating the different nerves with different electrical signals having different waveforms, amplitude, current, and the like, it is possible to induce different sensations. For example, the Merkel cell 14 receptors may encode pressure through firing frequency. Thus, by stimulating a Merkel cell 14 receptor with a variety of different electrical impulses of different frequencies, it may also be possible to induce sensations of touch of a hard object and/or touch of a soft object. For further example, a Meissner corpuscle 12 may be stimulated to elicit a stable vibratory sensation. Moreover, stimulation of the Pacinian corpuscle 18 may facilitate the generation of location-shifted stimuli, meaning the perceived stimulus is perceived to be at a different location that the electrode applying the electrical stimuli. Thus, any and all perceptible aspects of tactile stimulation may be evoked, in addition to unique, non-tactile stimulation.

A user may learn to associate meaning with each sensation, thereby facilitating communication with a user. The system and method may provide a sequence of such sensations in parallel, and in series over time. Moreover, a user may be readily trained to recognize the sequence of such sensations as corresponding to meanings. In various embodiments, a wearable headpiece, such as glasses with a built-in visual image projector may be worn and visual images may be projected that correspond to different electrical stimuli. The user may thus be trained to understand the meaning of the different electrical stimuli by being shown relevant visual images. A user may also enjoy training through use of a smartphone app, or a computer program, or an online training portal. For example, a computer application may be loaded on a computer and screen displays may correspond to different electrical stimuli. Yet furthermore, augmented reality, virtual reality, and other such immersive environments may be created by the combination of a visual stimuli and an electrical stimuli. Still yet furthermore, bone conduction headphones or other aural stimulus devices may be incorporated into the glasses to further provide auditory stimuli in connection with the electrical stimuli. In this manner, stimulation of vision, sound, and tactile senses may be combined to communicate information or simulate seen, heard, and felt experiences.

Many example use cases may be contemplated. In one example embodiment, an application is installed on a handheld computing device such as a smartphone. The application may connect the smartphone to the worn device providing the electro-tactile stimulation to the user's nerves. For instance, text messages, alarms, and other alerts that would generate a visual or audible alert at the handheld computing device may generate a tactile alert via the system and methods herein. An application may also be run on a desktop or laptop computing device. The application may connect the computer to the worn device providing the electro-tactile stimulation to the user's nerves. For instance, training scenarios, games, and other visual displays on the computer may correspond to tactile alerts. In this manner, a user may be trained to understand the meaning of different alerts in an immersive electronic training environment, through scenario-based training episodes, and the like.

Moreover, multiple devices may provide tactile information to multiple body areas. For instance, multiple finger rings, toe rings, bracelets, and/or other devices may be used. The different devices may play different communicative roles. For example, a ring may be placed on a first finger and a second finger. Upon receipt of a message, both rings may stimulate one or more nerve to indicate the presence of an alert, subsequently one ring may stimulate nerves to communicate the nature or origin of the alert, and another ring may stimulate nerves to communicate content of the alert.

Systems and methods to communicate via such stimuli may also contain aspects to receive user input. For instance, a ring that electrically stimulates nerves may also include a touch sensor that receives inputs. For instance, human input to the system or method may include swipes, taps, multi-taps, deep taps, voice dictation, motion or gesture tracking (e.g., via gyroscopic, piezoelectric, optical, magnetic, radio frequency, and/or other sensors).

Users thus may readily translate conversations with foreign language speakers, receive and understand navigation instructions from a mapping device without looking at the device or otherwise becoming visually distracted, may control devices, may learn languages, may control game systems, may engage in virtual reality environments, and may conduct financial transactions, among other uses, without need for engaging vision or hearing senses.

Figure 2:
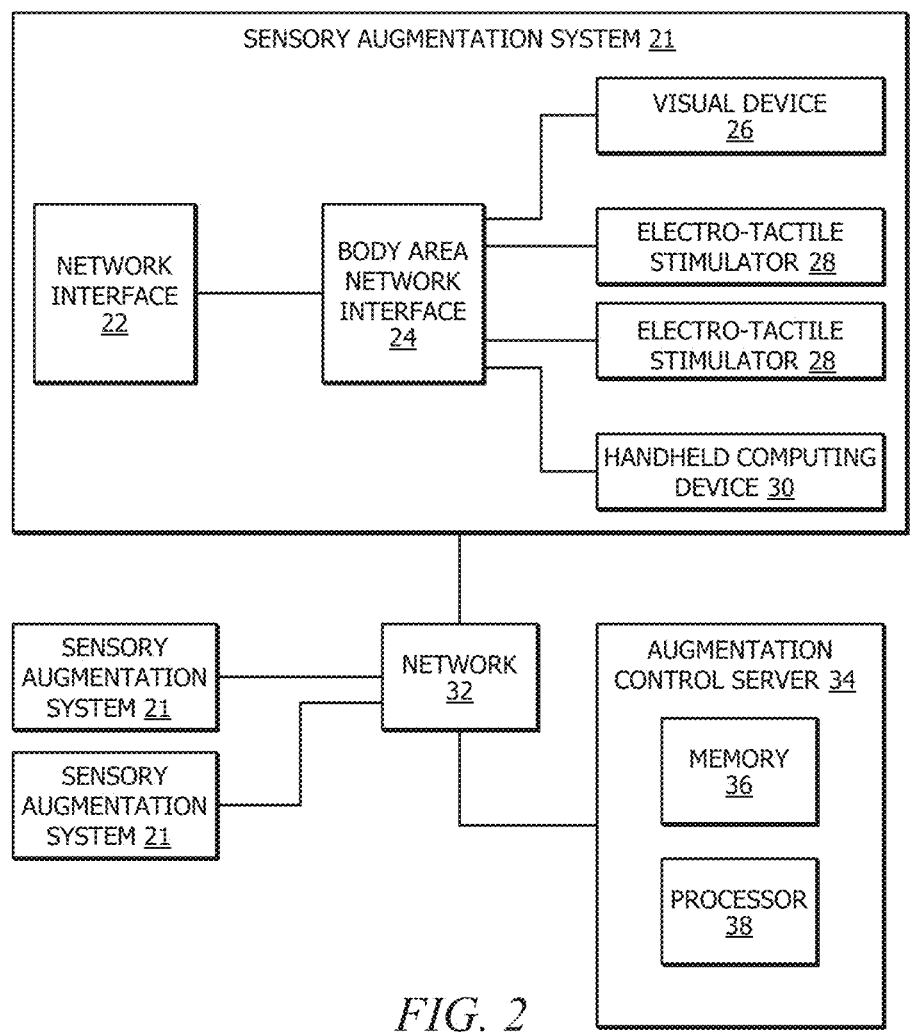
FIG. 2 is an example sensory augmentation platform able to communicate with human nerves in accordance with aspects of the disclosure.

With reference now to FIG. 2, a sensory augmentation platform 20 is disclosed. The sensory augmentation platform 20 may include one or more worn sensory augmentation system 21. The sensory augmentation platform 20 is configured to communicate human readable data to a user via electro-tactical stimulation, such as by interacting with at least some of the nerves illustrated and described with reference to FIG. 1. In various instances, the sensory augmentation platform 20 is also configured to receive inputs from a user via various devices or sensors discussed more fully herein. The sensory augmentation platform 20 may comprise wearable aspects and may comprises remote servers, databases, handheld devices, and combinations thereof.

As mentioned, the sensory augmentation platform 20 may include one or more worn sensory augmentation systems 21. A sensory augmentation system 21 comprises a worn apparatus configured to delivery electrical stimulation to nerves in order to communicate human-readable messages through the stimulation. In various instances, a sensory augmentation system 21 has multiple separate components. For example, a sensory augmentation system 21 may incorporate an existing smartphone, or multiple different worn devices. In various instances, a sensory augmentation system 21 may comprise a ring. In further embodiments, a sensory augmentation system 21 may comprise a bracelet, a wrist watch or wrist watch band, an earring, a necklace, or any other worn device as desired. Moreover, a sensory augmentation system 21 may be integrated into an item of apparel. For example, a sensory augmentation system 21 may be integrated into a headset, or eyeglasses, for instance, in an ear clip of eyeglasses. In further instances, a sensory augmentation system 21 may be integrated into clothing such as woven into or otherwise incorporated into a sock, or a shoe, or other footwear, as desired.

A sensory augmentation system 21 may be in electronic communication with a network 32. For instance, a sensory augmentation system 21 may be connected to the internet. The sensory augmentation system 21 may communicate with other sensory augmentation systems 21 via the network 32. For example, multiple individuals may wear a sensory augmentation system 21 which may be connected to the network 32. The individuals may send and receive messages to/from the sensory augmentation system 21 of each other. Furthermore, a user may wear multiple sensory augmentation systems 21. While in some embodiments, multiple sensory augmentation systems 21 of a user may intercommunicate via a local network or virtual local area network, such as via local Bluetooth connections to a user's smartphone, in further instances, multiple sensory augmentation systems 21 of a user may both connect to a network 32 such as the internet and may intercommunicate via the network 32. Thus, the multiple sensory augmentation systems 21 shown in FIG. 2 may be associated with different individuals, or multiple of the multiple sensory augmentation systems 21 shown in FIG. 2 may be utilized by a same individual.

In various embodiments, the sensory augmentation systems 21 may be in electronic communication, via a network 32, with an augmentation control server 34. In various instances, the augmentation control server 34 provides data to the sensory augmentation system 21 representative of a message to communicate to a user via electrical stimulation. Moreover, in various instances, the augmentation control server 34 receives data from a user, such as via data input aspects of a sensory augmentation system 21, for processing in connection with messages, and/or for communication to a further user of a further sensory augmentation system 21.

Each sensory augmentation system 21 may communicate with the augmentation control server 34 and the augmentation control server 34 may permit or reject forwarding of the message to a different sensory augmentation system 21. In this manner, the sensory augmentation system 21 may transmit information, receive information, and interact with other sensory augmentation systems 21, as desired. In various embodiments, a user may wear two sensory augmentation systems 21, or may wear a sensory augmentation system 21 with multiple worn components to electrically stimulate multiple parts of a user's body. The augmentation control server 34 may coordinate the provision of messages to the multiple sensory augmentation systems 21 to be delivered in a time-coordinated manner to a user. In further instances, a local device of the user coordinates the provision of messages to the multiple sensory augmentation systems 21 to be delivered in a time-coordinated manner to the user. For instance, one or more of the sensory augmentation systems 21 may effectuate such coordination.

With ongoing reference to FIG. 2, the worn sensory augmentation system 21 is now discussed in greater detail. The worn sensory augmentation system 21 may comprise multiple aspects, some of which may be housed in a same enclosure and some of which may be housed in different enclosures. For example, a sensory augmentation system 21 may include a ring. In further instances, a sensory augmentation system 21 may include two rings worn on different fingers. Moreover, the sensory augmentation system 21 may include a smartphone (computing device 30) connected to the two rings, such as via a Bluetooth connection.

The worn sensory augmentation system 21 may comprise a body area network interface 24. The body area network interface 24 may provide the Bluetooth or other connection that connects aspects of the sensory augmentation system 21 in operative communication. In various instances, the body area network interface 24 includes an aspect of a computing device 30, whereas in further instances, it is a separate device. The body area network interface 24 may provide a Bluetooth, Wi-Fi, near-field communication (NFC), WiMAX, 802.11x, ZigBee, cellular or other electrical, optical, sonic, or other operative connection between aspects of the sensory augmentation system 21. The body area network interface 24 may receive input from other aspects of the sensory augmentation system 21 and may provide output to other aspects of the sensory augmentation system 21. One such aspect may include a network interface 22.

A network interface 22 of a sensory augmentation system 21 may comprise an electronic modem or other communication device. For instance, the network interface 22 may be a transceiver configured to connect the sensory augmentation system 21 to a network 32. In various instances, the network interface 22 may comprise a Bluetooth, Wi-Fi, WiMAX, 802.11x, ZigBee, cellular, or any other interface operative to connect the sensory augmentation system 21 to a network 32, such as the Internet. The network interface 22 may be an aspect of another component of the sensory augmentation system 21, such as an aspect of a computing device 30. Moreover, the network interface 22 may be an aspect of the electro-tactile stimulator 28.

The sensory augmentation system 21 may include a visual device 26. A visual device 26 comprises a device configured to generate visual images for a user to view. For example, a visual device 26 may comprise a heads-up display of a pair of worn glasses. In further instances, visual device 26 is a screen of the computing device 30. In various instances, text, photos, images, or other visual indications are provided to a user, by the worn sensory augmentation system 21, such as to provide for mapping, augmented reality, or other visual services. Moreover, because a user may be unfamiliar with the meaning of different electro-tactile stimuli, a representative image may accompany each stimulus, or at least some stimuli. Also, in various training scenarios, the sensory augmentation system 21 may, via a network interface 22 or a body area network interface 24, connect directly to a computing device, such as a computer or a smartphone. The computer or smartphone may run a training application, such as a game, scenario-based training program, tutorial, or other application whereby a user is trained to interact with the sensory augmentation system 21. For example, the sensory augmentation system 21 may provide electrical stimuli to a finger representing a variety of different characters or words, while showing images of the relevant character or word on the visual device 26.

The sensory augmentation system 21 may include an electro-tactile stimulator 28. The electro-tactile stimulator 28 is a worn article that provides electrical signals to stimulate a wearer's body, providing signals with different characteristics so that meaning may be communicated thereby. For example, the electro-tactile stimulator 28 may comprise a ring. In various instances, two electro-tactile stimulators 28 are implemented. For instance, a sensory augmentation system 21 may include a ring worn on each hand, e.g., a first electro-tactile stimulator 28 and a second electro-tactile stimulator 28.

The electro-tactile stimulator 28 may be configured to deliver a variety of different electrical stimuli. With reference to both FIGS. 2 and 3, an electrical signal may be passed between one or more electrodes 43 of the electro-tactile stimulator 28. Moreover, multiple electrical signals may be passed between or among multiple electrodes 43 of the electro-tactile stimulator 28. Thus, an electro-tactile stimulator 28 may have at least one electrode array 42 driven by an electrode driver 40 (discussed below) and contactable to a human body to provide electrical stimulation having a first stimulation waveform, such as providing the electrical stimulation perceptible by nerves of the human body as illustrated and described with respect to FIG. 1. The electrical signals (stimulation waveform) may be varied in frequency, waveform (e.g., square wave, triangle wave, sine wave, varying waveform, DC, etc.), voltage, current, duty cycle, and or the like. Moreover, the role as anode or cathode, of different electrodes 43 may be changed and the polarity of the electrical signal(s) changed over time. Furthermore, different electrical signals may be delivered in parallel or in sequence, and combined. Yet furthermore, electrodes 43 may be spaced, and different electrodes 43 may be energized with different electrical signals (different stimulation waveforms). In addition, electrodes 43 may be selectively driven so that spatial sensations (e.g., the perceived origin of the electrical stimulation) in addition to the character of the sensation itself may be changed to communicate different messages. Communicated messages may include representations of text, images, graphics, memes, phonemes, calculations, sounds, emoji, and/or any other information able to be received through other human senses.

Consequently, a user may be able to feel electrical stimulus with pinpoint accuracy at different locations on the body, the locations corresponding to different information. For instance, electrical stimulus may be felt at different positions around a finger proximate to an interior annulus of a ring having the electrode array 42. By registering the different clock positions of the electrical stimulus, perceived with pinpoint accuracy, a user may register different messages.

Similarly, a user may feel different sensations arising from the electrical stimulus, the different character of the sensations corresponding to different information. For example, the electrical stimulus may provide different sensations of hardness, softness, pressure, vibration, and/or any other mechanical or non-mechanical sensory input, as well as different combinations thereof. The different sensations may correspond to different information communicated to the user and may be combined with stimulus perceived to be at different locations, thereby communicating yet further varieties of complex information.

Finally, the sensory augmentation system 21 may include one or more computing device 30. The computing device 30 may be a smartphone, a tablet, a wearable computer, a portable computer such as a laptop, or any other computing device 30 as desired. In various embodiments, the computing device 30 is an integrated processor of the electro-tactile stimulator 28. Moreover, the body area network interface 24 and the network interface 22 may be a portion of the computing device 30 and/or the electro-tactile stimulator 28. In yet further instances, the body area network interface 24 is omitted and the network interface 22 also performs the function of the body area network interface 24. Moreover, in various embodiments, the electro-tactile stimulator 28 connects directly to the computing device 30 so that one appreciates that the body area network interface 24 is an aspect, such as a Bluetooth transceiver, of the computing device 30. Similarly, the network interface 22 may be an aspect of the computing device 30.

In various embodiments the computing device 30 thus provides the body area network interface 24 and the network interface 22 and is operatively connected to the electro-tactile stimulator 28 and the visual device 26 by a wireless technology. In yet further embodiments, the computing device 30, the body area network interface 24 and the network interface 22 are all incorporated into the visual device 26. For instance, the visual device 26 may be a wearable pair of glasses with a computer therein.

The computing device 30 provides processing power and memory for the electro-tactile stimulator 28. For instance, the electro-tactile stimulator 28 may be small, and/or power efficient, such that processing tasks are offloaded to a connected device, such as the computing device 30. In this manner, battery life may be improved and the form factor may be miniaturized for the electro-tactile stimulator 28.

This processing power provided by computing device 30 may be used for a variety of purposes. For instance, data may be structured and rearranged to be suitable for provision to an electro-tactile stimulator 28. For example, a user may wish to read a text message from a friend via electrical stimulation signals provided to a finger by an electro-tactile stimulator 28 connected to that finger. The computing device 30 may process the text message character-by-character or word-by-word to generate symbols for delivery via electro-tactile stimulation. These symbols may be then provided by the computing device 30 to one or more of the electro-tactile stimulators 28 in sequence or parallel. Moreover, the computing device 30 may set the delivery rate of the stimulation, for instance, depending on a user's proficiency in interpreting electro-tactile messages. Further, and as mentioned above, in addition to text, any human perceptible information desired to be communicated may be translated to corresponding electrical stimuli. For instance, sounds, emoji and other representative characters, scents, graphics, and/or the like may be associated with a particular sensation or set of sensations communicable via electrical stimuli.

Figure 3:
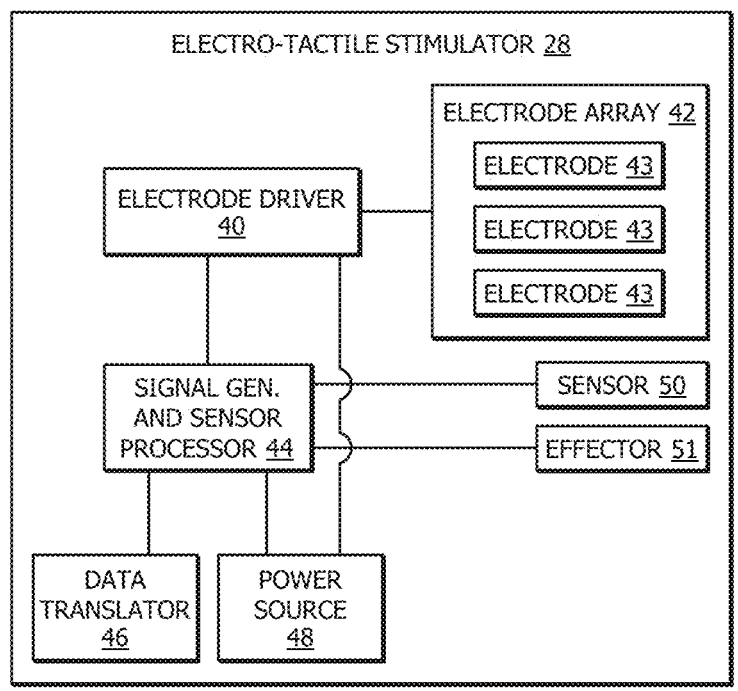
FIG. 3 is an example block diagram of an electro-tactile stimulator of the sensory augmentation platform depicted in FIG. 2 in accordance with aspects of the disclosure.

Having discussed the sensory augmentation system 21, attention is turned to the electro-tactile stimulator 28 more specifically. With reference to FIG. 3, an electro-tactile stimulator 28 may comprise a data translator 46. A data translator 46 may receive data from a body area network interface 24. For example, data may be received that corresponds to one or more instances of electrical stimulation to be provided to a user. The data translator 46 receives this data and interprets it to generate electrical stimulation with characteristics provided according to the data. The data translator 46 is connected to a signal generation and sensing processor 44 and provides this data thereto in a form suitable for the signal generation and sensing processor 44.

The electro-tactile stimulator 28 may comprise a signal generation and sensing processor 44. The signal generation and sensing processor 44 may be an embedded computing device, a processor and memory, or any other programmable electronic device or circuit configured to receive data from the data translator 46 and to send control signals (an "instruction" or a "driving instruction") corresponding to this data to an electrode driver 40. Similarly, the signal generation and sensing processor 44 may receive signals from one or more sensor 50 corresponding to that which the sensor 50 senses, and may provide this data to the data translator 46 for packaging in an appropriate structure to deliver to the body area network interface 24 (FIG. 2). For instance, the sensor 50 may be a heartrate sensor and may provide heartrate data to the signal generation and sensing processor 44 for provision to the body area network interface 24 (FIG. 2), and transmission to another device for storage and processing, for instance, the computing device 30 (FIG. 2) and/or the augmentation control server 34 (FIG. 2).

Figure 4:
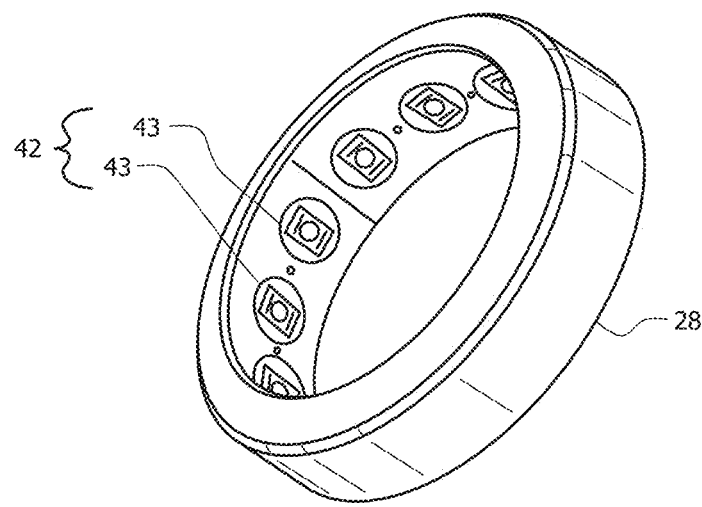
FIG. 4 is an example wearable ring including example electro-tactile stimulators in accordance with aspects of the disclosure.

In various embodiments, sensor 50 comprises one or more touch sensor. The one or more touch sensor 50 may facilitate data entry via the electro-tactile stimulator 28. For instance, the electro-tactile stimulator 28 may comprise a worn ring. A user may manipulate a surface of the ring to communicate information for transmission to another device for storage and processing. For instance, a user, receiving a message via electrical stimuli, may desire to respond by transmitting a responsive message. A series of swipes (e.g., up, down, left, right, diagonal, etc.) on one or more touch sensor, and/or a series of taps on one or more touch sensor, and/or a series of shakes, vibrations, hand motions (such as sign language), and/or the like may correspond to human readable message elements, such as characters, words, phonemes, emojis and/or the like. A user may stimulate one or more touch sensor such as by forming a hand having the ring into a fist, and using a finger of another hand to touch the external annular surface of the ring. In various embodiments, multiple sensors 50 are disposed about the exterior annular surface of a ring, similar to the disposition of the electrodes 43 on an interior annular surface of the ring. For example, FIG. 4 shows an example implementation of the electro-tactile stimulator 28 with electrodes 43 disposed about the exterior annular surface. For ease of viewing, the reference numbers 43 are only shown in connection with some of the electrodes 43 of an electrode array 42 of the electro-tactile stimulator 28 of FIG. 4. The disposition of electrodes 43 is further shown in FIGS. 7A-7F. In further instances, sensor(s) 50 may be motion sensors capable of detecting movement. For example, a user may perform sign language gestures which are detected by the motion sensors. It is contemplated that a user may communicate with similar speed as typing a text message, or faster speed via input to sensor(s) 50.

The electro-tactile stimulator 28 may include one or more effector 51. An effector 51 comprises an additional human-readable communication mechanism, such as a vibration device. In various embodiments, the electro-tactile stimulator 28 may further effectuate tactile stimulation through mechanical movement, in addition to the ability to interact electrically with nerves. The effector 51 may comprise a visual indicator, such as a light source, or an electronically-controlled display or pattern provided by an LCD display, electronic ink and/or any type of human perceptible indicator as desired. The effector 51 may further comprise non-human readable mechanisms, such as a NFC enabled device configured to effect financial transactions, operate as a key to control access to limited access areas and/or any other function as desired.

The electro-tactile stimulator 28 may include a power source 48. A power source 48 comprises a source of electrical energy. The power source 48 may be a battery, or a super capacitor. The power source 48 may include a charger, such as to harvest RF energy, body heat, motion of the user, and/or the like. The power source 48 may include an inductive charger, such as to facilitate recharging of a battery or super capacitor by exposure to an electromagnetic field.

The electro-tactile stimulator 28 may include an electrode driver 40. An electrode driver 40 may be connected between the signal generation and sensing processor 44 and the electrode array 42. The electrode driver 40 may receive control signals (an "instruction" or a "driving instruction") from the signal generation and sensing processor 44 corresponding to one or more electrical waveform with which to excite one or more electrode of the electrode array 42. Because the electrode array 42 typically will require a higher voltage electrical waveform than many microprocessors generate, in various embodiments, the electrode driver 40 generates the driving waveform of the electrodes 43 of the electrode array 42 in response to the driving instructions, rather than the signal generation and sensing processor 44 being directly connected to the electrode array 42. The electrode driver 40 may comprise an H-bridge, or a buck/boost converter, or one or more capacitors for discharging, or one or more transformers, coils, and/or the like.

Finally, the electro-tactile stimulator 28 comprises an electrode array 42. An electrode array 42 comprises one or more electrodes 43 contactable to a human body to provide electrical stimulation. In various embodiments, multiple electrodes 43 comprise a current source and one electrode comprises a current sink. In further embodiments, multiple electrodes 43 comprises a current sink. In various embodiments, a single electrode 43 comprises a current source and multiple electrodes 43 comprise a current sink. In further embodiments, multiple electrodes 43 comprise the current source. Thus, one may appreciate that different combinations of electrodes 43 may be selectively excited in different patterns and with signals of different voltage, current, waveform, frequency, and/or the like so that different sensations are perceived by the user and thus can be translated by the user's nervous system into different messages. For example, a long pulse followed by a short pulse followed by a long pulse, followed again by a short pulse may correspond to the character "C," whereas a short pulse followed by a long pulse may correspond to the character "A." More complex symbolic representations are possible due to the virtually infinite combination of pulse length, possibilities of which electrode 43 is stimulated, and possibilities of which combinations of electrodes 43 are stimulated, the voltage, current waveform, and frequency of each stimulation, both in sequence and in parallel, and/or the like.

Figure 5:
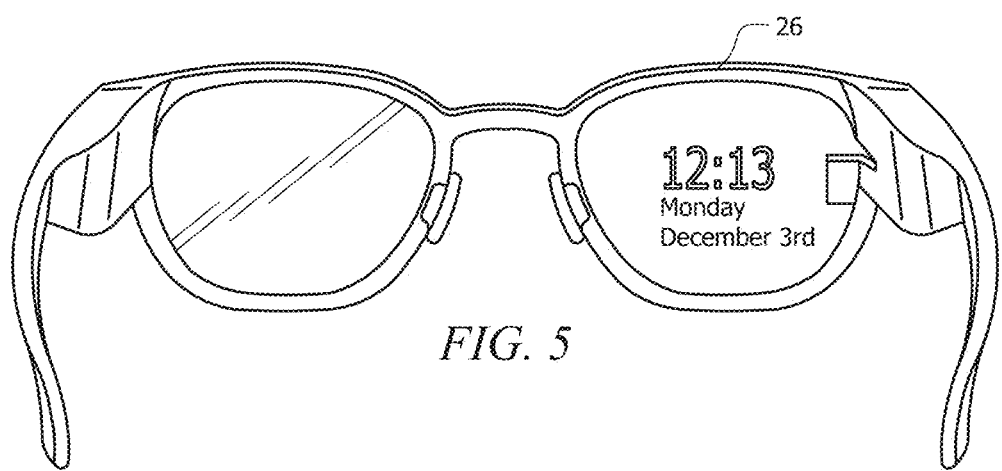
FIG. 5 is an example visual device operable in connection with an electro-tactile stimulator to provide visual information along with the electro-tactile stimulation in accordance with aspects of the disclosure.
Figure 6:
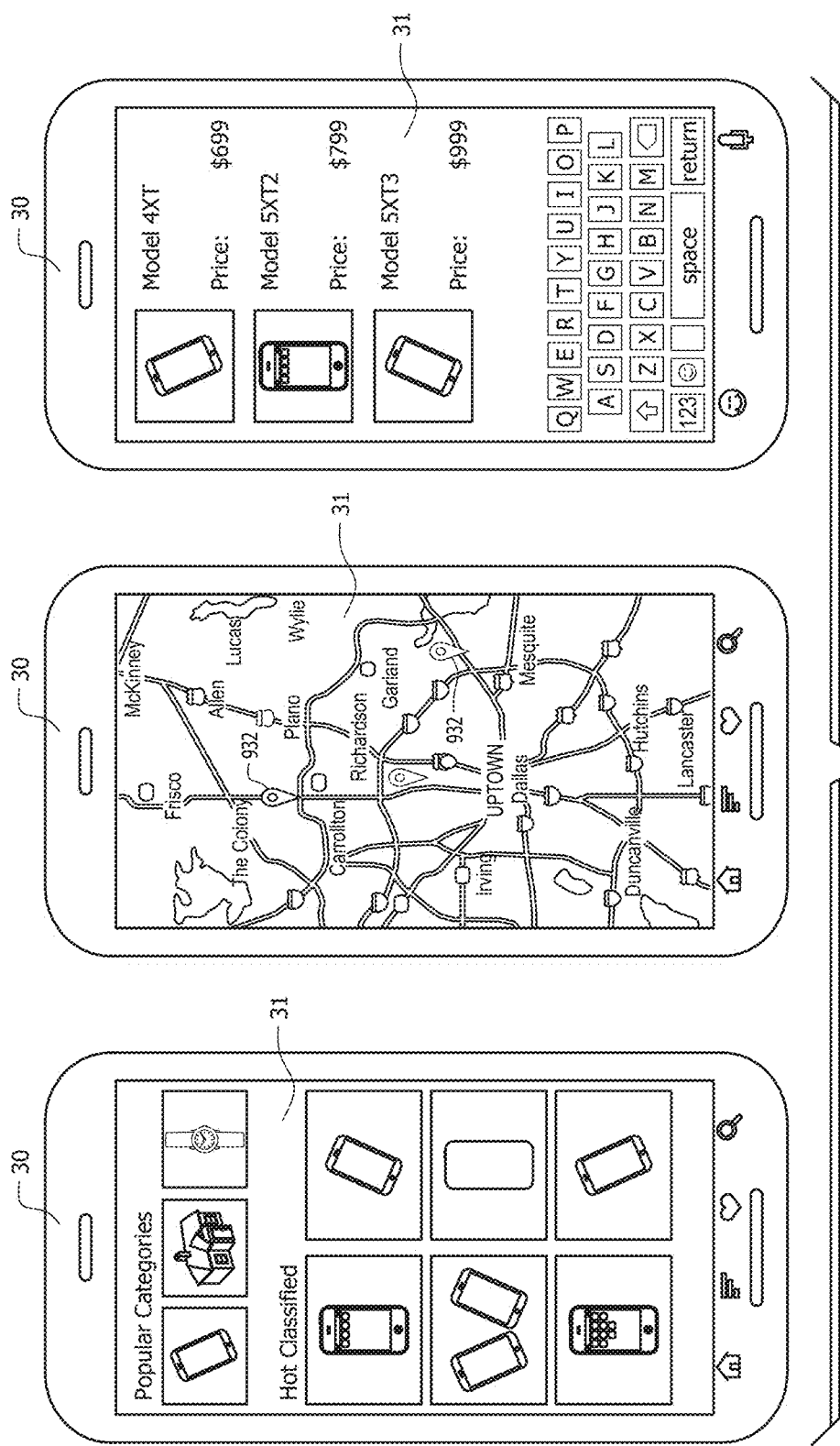
FIG. 6 is example screen displays of a handheld computing device operable in connection with an electro-tactile stimulator to provide content to be transmitted via human readable electrical stimulation in accordance with aspects of the disclosure.

This tremendous complexity of pulse combinations can present a possible learning challenge for a user. In various embodiments, the worn sensory augmentation system 21 comprises one or more visual devices 26 as mentioned above. With reference now to FIGS. 5 and 6, in various embodiments, the electro-tactile stimulator 28 comprises a ring, worn on a finger with multiple electrodes 43 of an electrode array 42 in contact with a user's finger. The user may also wear a pair of eyeglasses, shown in FIG. 5, having a built-in image projector (e.g., visual device 26 from FIG. 2) or any other circuitry suitable for presenting or providing an image. In various embodiments, images may be projected or otherwise provided or presented that correspond meaningfully to the electrical stimulation provided by the electrode array 42.

Visual device 26 may provide further functions. For instance, visual device 26 may provide any visual input corresponding to the electro-tactile input or complementary thereto. Visual device 26 may also provide unrelated input. For example, in various instances, visual device 26 may provide for augmented reality experiences. Visual device 26 may provide for overlaid textures on a surrounding environment of a user. For example, visual device 26 may provide for projection of images corresponding to textures that overlay perceived real-world items. For instance, a smooth surface may, when looked upon by a user of visual device 26, be made by visual device 26 to appear rough or otherwise augmented by digital assets. Various visual augmented reality experiences may be combined with electro-tactile stimulation to further communicate related information to a user through both visual and electro-tactile stimulus.

Directing attention now to FIG. 6, example screen displays 31 of a computing device 30 are depicted. In various embodiments, a user may desire to receive content displayed visually on the computing device 30 in a non-visual medium. For instance, a user may desire to receive this content through electrical stimulation. In various embodiments, a computing device 30 may transmit via the body area network provided by the body area network interface 24 (shown in FIG. 2), signals to the electro-tactile stimulator 28 (shown in FIGS. 2 and 3) corresponding to content of a screen display 31 for communication to a user. The electro-tactile stimulator 28 receives the data corresponding to this content and generates a sequence of electro-tactile stimulation waveforms that are provided to the user's body, such as to a finger. In this manner, content displayed by the computing device 30 may be provided by the electro-tactile stimulator 28.

Turning now to FIGS. 7A-7F, and with ongoing reference to FIGS. 2-3, an example use case of an electro-tactile stimulator 28 is shown. In FIGS. 7A-7F, the electro-tactile stimulator 28 comprises a ring with an electrode array 42 comprising electrodes 43 on the inside surface of the ring. In some examples, the electrodes 43 may be evenly spaced around the interior annulus of the ring. In other examples, the electrodes 43 may be unevenly spaced. Moreover, two rings may be used so that two electro-tactile stimulators 28 are controlled in concert. For instance, one electro-tactile stimulator 28 may communicate to the user the nature and character of the content presently or imminently communicated by the other electro-tactile stimulator 28. For instance, one electro-tactile stimulator 28 may communicate to the user that an incoming text message has been received, while the other electro-tactile stimulator 28 may communicate the content of the text message simultaneously or imminently thereafter.

The electrode array 42 may comprise twelve electrodes 43. In further instances, any number of electrodes 43 may be selected. The electrodes 43 may correspond to different locations around the ring. With specific focus on FIGS. 7A-B, an electrode array 42 comprising twelve electrodes 43 is shown. For ease of viewing, the reference numbers 43 are only shown in connection with some of the twelve electrodes 43.

In various instances, a English word is desired to be communicated to a user. For instance, the world "APPLE" is desired to be communicated. While the electrodes 43 may communicate symbols, phonemes, or any other communicative device representable by electrical stimulation, in this non-limiting example, individual characters are communicated in sequence to comprise a word. For instance, FIG. 7B shows three electrodes 43 being energized. The electrodes 43 correspond to vertices or other index points on a represented character. For instance, for the letter A, electrodes 43 at positions 0, 7, and 5 may be energized. The number associated with the electrode corresponds to its clock position in this example, so the electrodes 43 at the 12 o'clock, 5 o'clock, and 7 o'clock positions are activated, corresponding to the three ends of the letter "A". At a second moment in time, a different set of electrodes 43 may be activated to correspond to the second letter in the word, "APPLE." While this disclosure generally discusses communication of an English word, in various other examples, any suitable language or character set is possible for communication according to this disclosure.

Figure 7A:
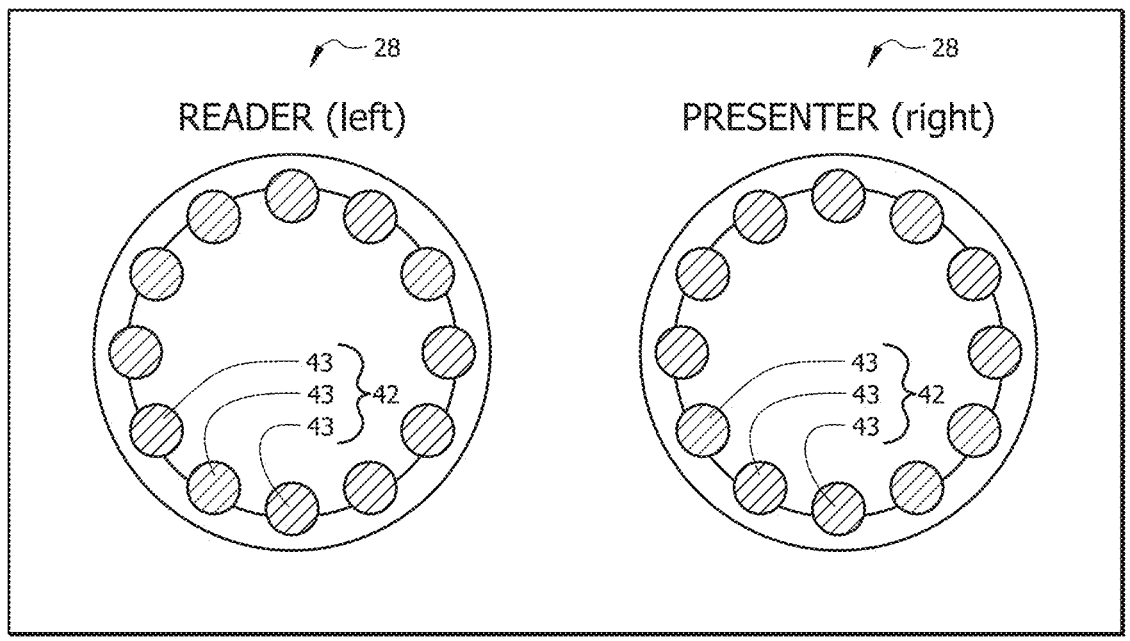
FIG. 7A is diagram of example electrodes of an electrode array for an electro-tactile stimulator in accordance with aspects of the disclosure.
Figure 7B:
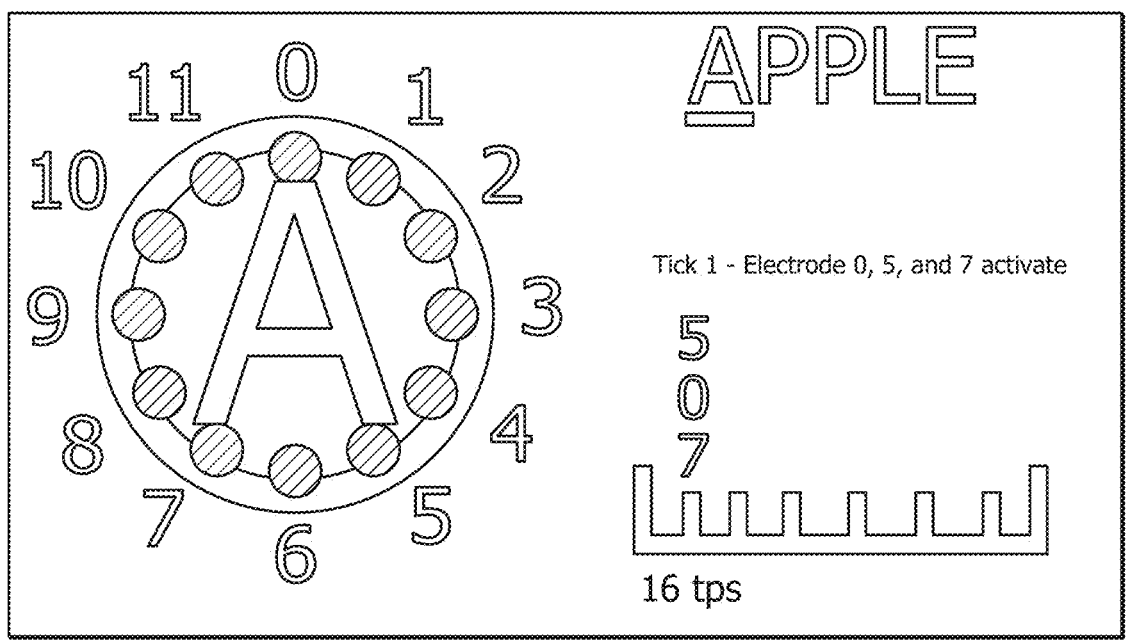
FIGS. 7B-7F are diagrams of an example schema for communicating a multi-character English word to a user by activating different electrodes of the electrode array in accordance with aspects of the disclosure.
Figure 7C:
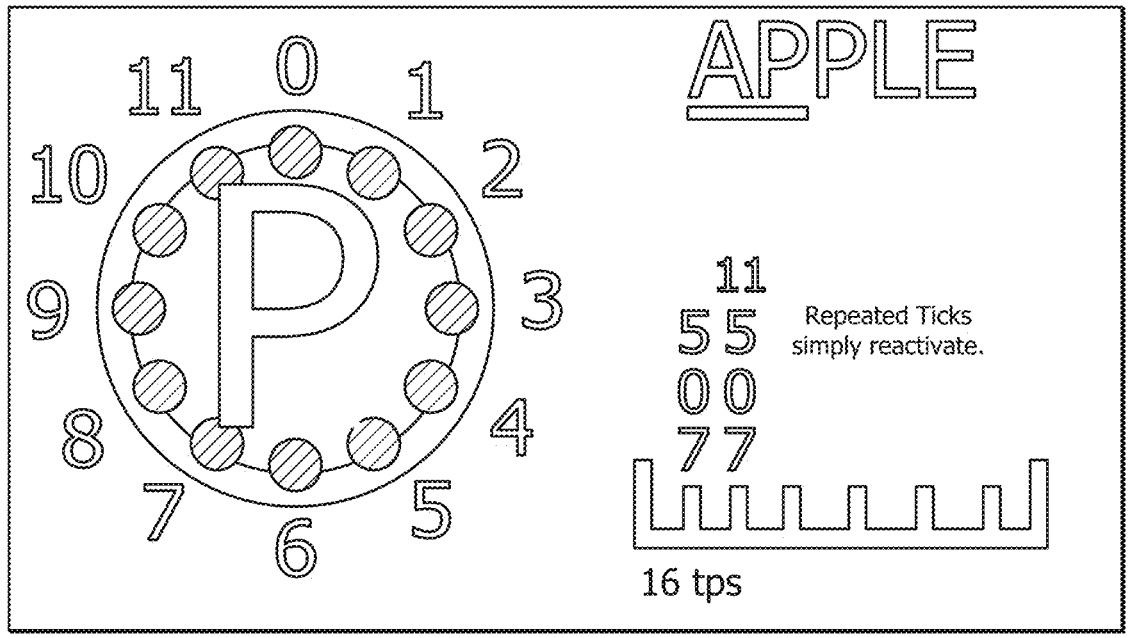

With reference to FIGS. 7A and 7C, electrodes 43 at positions 5 and 0 remain activated, and the electrode 43 at position 7 is momentarily pulsed off then back on, and the electrode 43 at position 11 is activated. In this manner, one may appreciate that the next letter, "P" is indicated, while the electrodes 43 associated with the first letter, "A," in some embodiments, remain activated to facilitate remembering by the user of the earlier character.

Figure 7D:
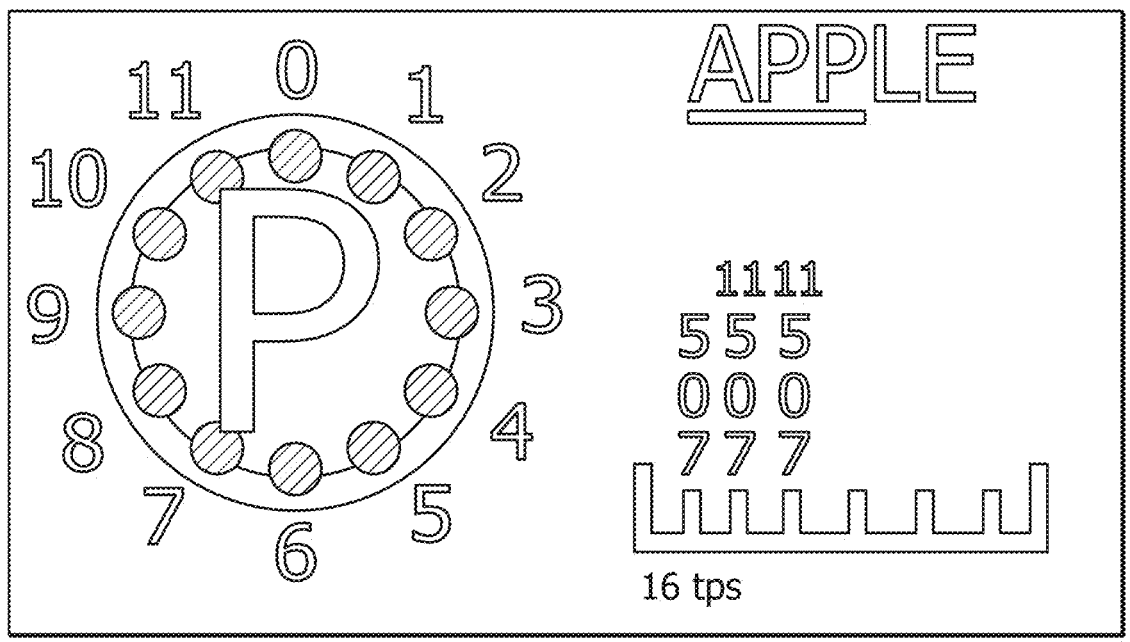

Turning now to FIGS. 7A and 7D, one may note that a second letter "P" is desired to be indicated. However, in order to indicate two identical characters in a row, a further temporal aspect is implemented. Specifically, the electrodes 43 corresponding to the letter P are pulsed off and then on again to represent a second sequential instance of the character. Electrodes 43 previously associated with the letter "A" and not with the letter "P" may be left remaining active and not pulsed.

Figure 7E:
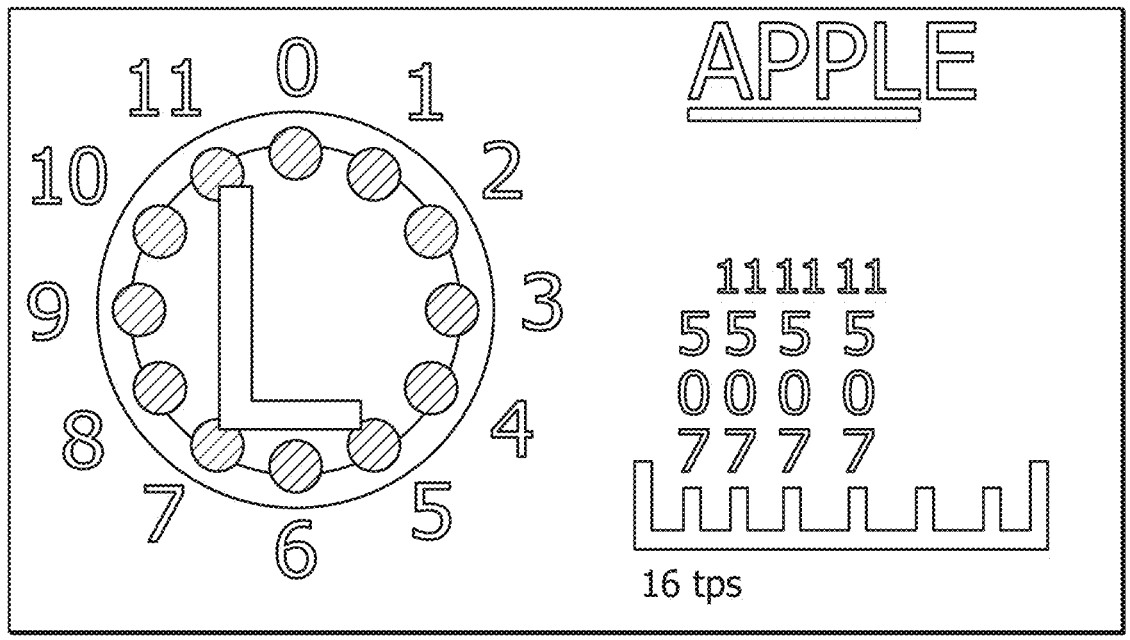

Subsequently, and with reference to FIGS. 7A and 7E, the next character, "L," is communicated. Electrodes 43 at positions 11 and 7 are pulsed off and back on, as these electrodes 43 were also associated with the letter "P" and the electrode 43 at position 5 is activated. The electrode 43 at position 0 has remained activated and is unchanged.

Figure 7F:
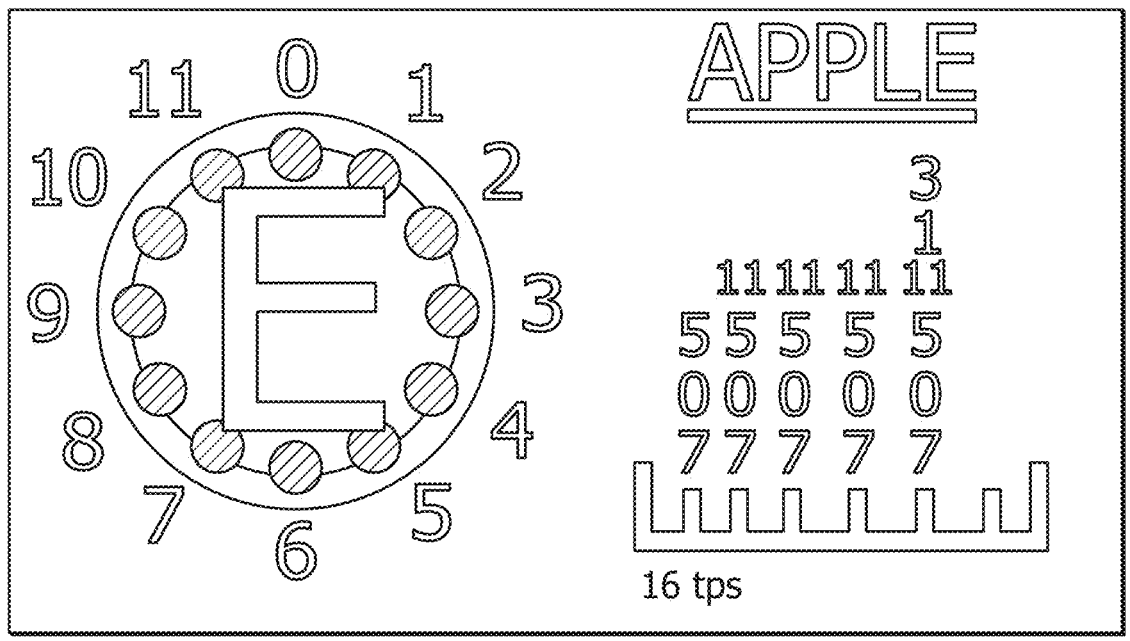

Finally, shifting focus to FIGS. 7A and 7F, the final letter, "E," is communicated. Electrodes 43 at positions 3, 1,11, 7 and 5 are all associated with the letter "E." Electrodes 43 at positions 11, 7, and 5 are pulsed off and back on, electrodes 43 at positions 3 and 1 are activated, and the electrode 43 at position 0 remains activated and is unchanged.

In various embodiments, each letter, character, phoneme, or other symbol is associated with an equal-duration period of time (a "tick"). Each tick maybe of a length sufficient to permit the user to identify the character, phoneme, or other symbol being communicated. Thus, the tick length may be shortened as a user gains proficiency. In various embodiments, following the final letter of a word or other collection of symbolically-represented information, all electrodes 43 are deactivated for a single tick, signaling the end of the word or other collection of symbolically-represented information. In other examples, all electrodes 43 may be activated, or any other programmed group of electrodes 43 may be activated and/or deactivated in any programmed pattern signaling the end of the word or other collection of symbolically-represented information. With reference to FIG. 7F, following the elapse of one tick for the final letter "E," each electrode may be deactivated for one tick (or other group of electrodes activated or deactivated in a programmed manner as described above), signaling the end of the word, prior to beginning presentation of subsequent user-readable stimuli.

Figure 8:
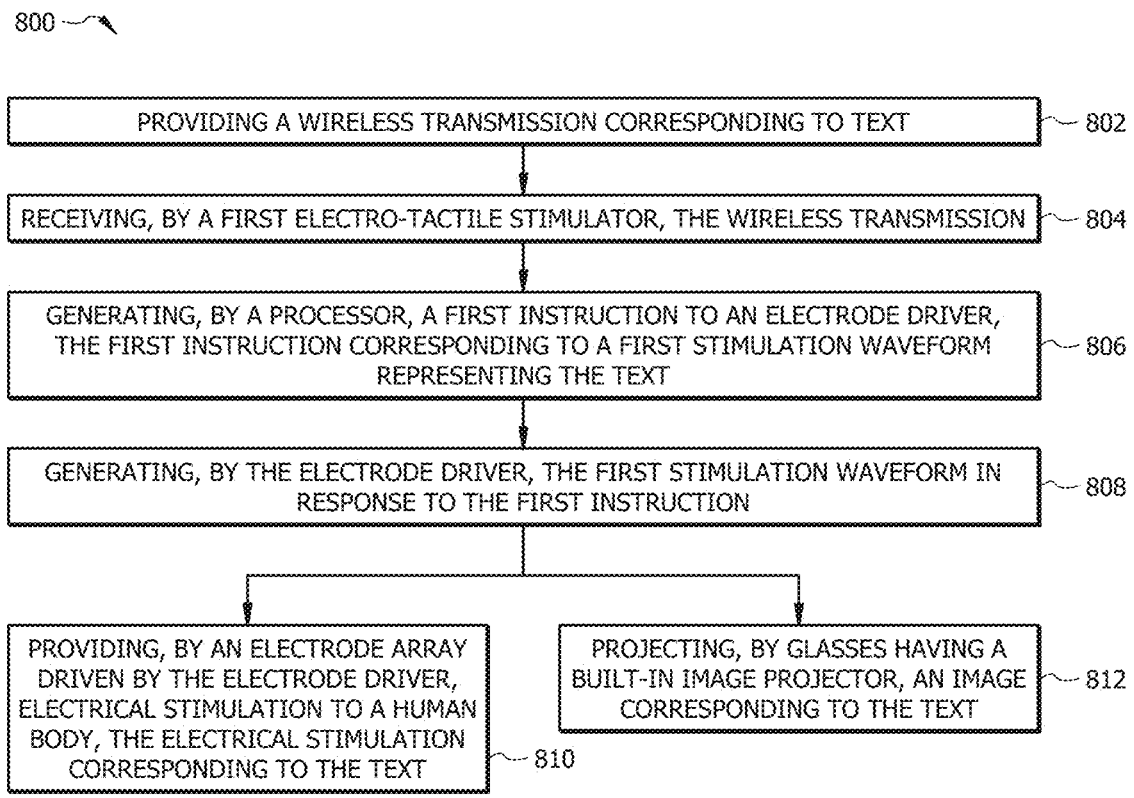
FIG. 8 is an example method of sensory augmentation in accordance with aspects of the disclosure.

Referencing FIG. 8, a method 800 of sensory augmentation is provided. The method 800 may be implemented in various parts by the augmentation control server 34, computing device 30, electro-tactile stimulator 28, and/or sensory augmentation system 21. The method may include providing, by a computing device, a wireless transmission corresponding to text (block 802). The method may include receiving by a first electro-tactile stimulator the wireless transmission (block 804). The method may further include generating, by a signal generation and sensing processor of the first electro-tactile stimulator, a first instruction to an electrode driver, the first instruction corresponding to a first stimulation waveform representing the text (block 806). The method may include generating, by the electrode driver the first stimulation waveform in response to the first instruction (block 808), and providing, by an electrode array driven by the electrode driver, electrical stimulation to a human body, the electrical stimulation corresponding to the text (block 810). In various embodiments, the method further includes projecting, by glasses having a built-in image projector, an image corresponding to the text (block 812).

Figure 9:
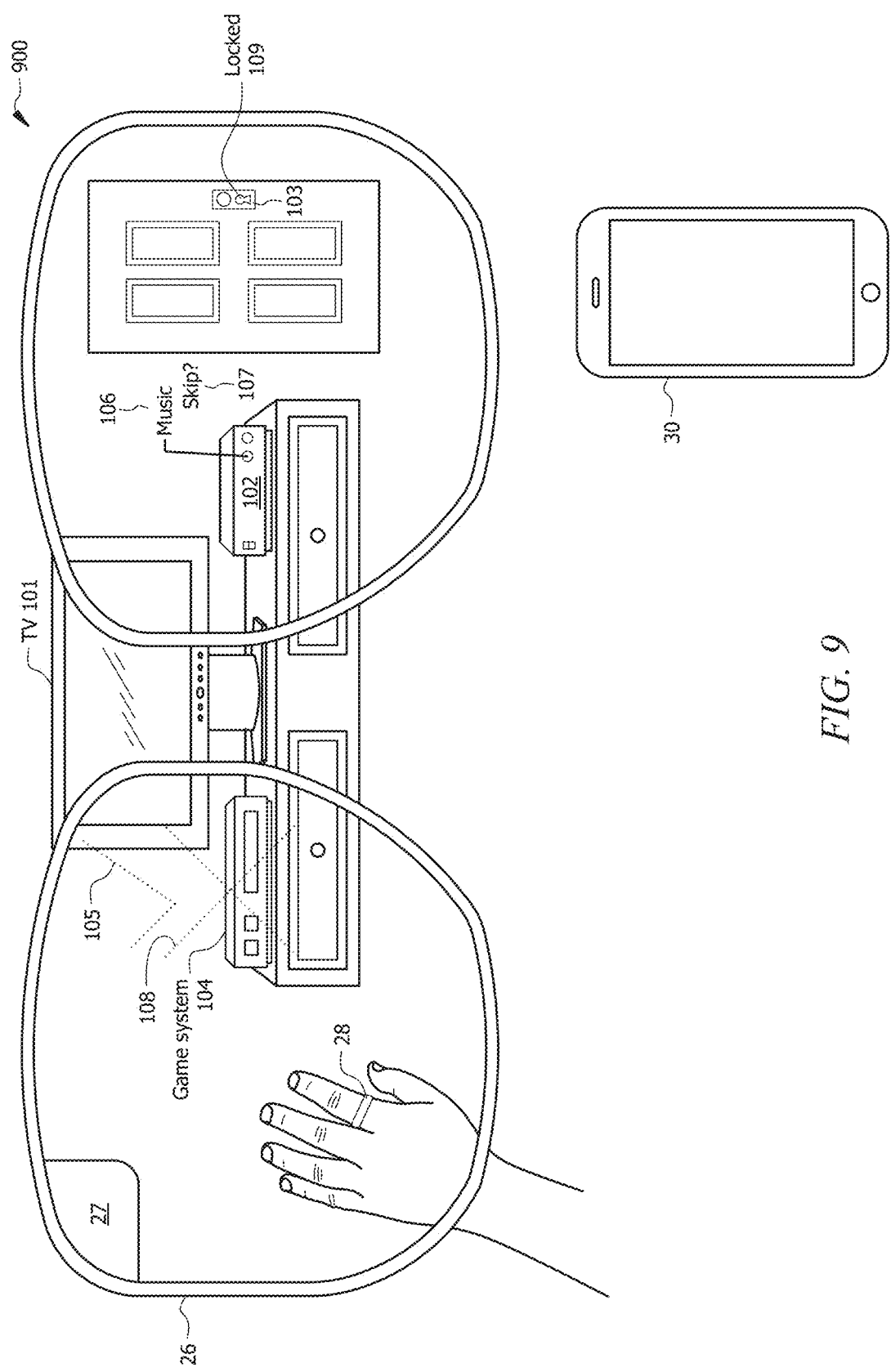
FIG. 9 is an example use scenario combining multiple aspects of the sensory augmentation system in accordance with aspects of the disclosure.

Referencing FIG. 9, and with additional reference to FIGS. 1-8 a use scenario 900 combining multiple aspects of the sensory augmentation platform 20 is shown. In various embodiments, a visual device 26 may further comprise sensor 27. Sensor 27 may comprise any sensor configured to register at least one of an absolute or relative location of an electro-tactile stimulator 28. For example, the sensor 27 may comprise a camera configured to visually identify the location of the electro-tactile stimulator 28. The sensor 27 may comprise a depth or distance sensor, for instance, an ultrasonic sensor. The sensor 27 may comprise an electromagnetic sensor sensing non-human visible spectrum. The sensor 27 may comprise any sensor configured to determine spatial information with respect to a surrounding environment of a user. Moreover, such sensed information may be implemented to facilitate identification of an absolute or relative location of a user, a user's head, a user's hand, a user's electro-tactile stimulator 28, and other objects. In yet further instances, sensor 27 is omitted and an inertial, gyroscopic, or other sensor (e.g., such as the sensor 50 described above) included in the electro-tactile stimulator 28 provides such data, for instance, data representative of an absolute or relative location of the electro-tactile stimulator 28. In either event, the sensory augmentation platform 20 is capable of determining at least one of a relative or an absolute location of the electro-tactile stimulator 28. Moreover, in either event, the sensory augmentation platform 20 (e.g., such as via the computing device 30) is capable of determining at least one of a relative or absolute location of objects in a surrounding environment of the user.

Consequently, the sensory augmentation platform 20 is able to ascertain hand movements by a user wearing the electro-tactile stimulator 28 on a finger or otherwise ascertain the positioning by the user of the electro-tactile stimulator 28. Thus, the sensory augmentation platform 20 may be capable to determine that a user is pointing, gesturing, or otherwise, through movement of the electro-tactile stimulator 28, providing relevant information input. In various instances, a user may point a hand with an electro-tactile stimulator 28 at a device desired to be controlled or otherwise interacted with via the sensory augmentation platform 20. For example, a user may point at a television 101 to turn the television on or off, or may gesture up or down or left or right to control channel and/or volume of the television 101. Moreover, the user may point or otherwise gesture to control many devices, or to query for a status of the device. For example, a user may point or otherwise gesture to control a game system 104, a smart home hub 102, an electronic lock 103 and/or the like. In various instances, the visual device 26 displays augmented reality data corresponding to a status of the television 101, game system 104, smart home hub 102, and/or electronic lock 103. In further instances, an application operating on a handheld computing device 30 depicts similar status information and/or permits control of the indicated devices. The visual device 26 may provide a television status indication 105 indicating that television 101 is on, and a game system indication 108 indicating that the game system 104 is off. Moreover, a lock status indication 109 may be depicted to allow ready determination of a locked or unlocked status of an electronic lock 103.

Furthermore, control aspects for devices may include both visual depictions via the visual device 26 and machine-human interactions by the electro-tactile stimulator 28. For example, the smart home hub 102 is shown playing music 106 and an option to skip a song is shown 107. A user may point, or otherwise interact with a point in space, such interaction detectable by the electromagnetic sensor 27 and/or by the electro-tactile stimulator 28, the point in space corresponding to a point in space overlaid by the projected text on the visual device 26 offering the option to skip 107. In response to a user pointing or touching such a point in space, the sensory augmentation platform 20 may interoperate with the smart home hub 102 via any suitable communication medium, directing it to take a responsive action such as to skip a song being played, etc. In at least some examples, the smart home hub 102 may be, may be a component of, may be co-housed with, or may otherwise share at least some computing resources with, the augmentation control server 34.

Thus, appreciating the teachings herein above and with reference to FIGS. 1-9 various use cases are possible. For instance, as mentioned, one or more sensor 27 on one or more visual device 26 may facilitate generation of a three-dimensional (3D) model of that which a user is looking at. Moreover, the electro-tactile stimulator 28 may be connected, directly or indirectly, to the visual device 26 or otherwise logically associated therewith. Consequently, a simulated, augmented, or virtual reality may be modeled. The modeled simulated reality may comprise a 3D representation of a surrounding environment of a user and movements of a user and/or a user's electro-tactile stimulator 28 within the surrounding environment. In various embodiments, this modeled simulated reality may be electronically combined with further modeled simulated realities of further users of further electro-tactile stimulators 28 and/or visual devices 26.

Consequently, not only may a user interact with aspects of a surrounding environment via a visual device 26 and/or electro-tactile stimulator 28, but a user may interact with aspects of a surrounding environment of a different user, via a visual device 26 and/or electro-tactile stimulator 28. For instance, a visual device 26 may project images corresponding to a surrounding environment of a different user, or a simulated surrounding environment that is virtual in nature, thereby facilitating interaction with virtual realities. For instance, an architect and a customer may each wear a visual device 26 and one or more electro-tactile stimulator 28. The architect may invite the customer to enter a simulated surrounding environment comprising an electronic model of a proposed building designed by the architect, or may invite the customer to interact with simulated items such as architectural plans and/or the like projected on the visual device 26.

A user may interact with a simulated environment or an environment of a different user via gestures or inputs measured by the electro-tactile stimulator 28. Moreover, once such an environment is mapped by the visual device 26, a user may continue to interact with the environment via an electro-tactile stimulator 28 even without wearing the visual device 26. For instance, an electro-tactile stimulator 28 may contain one or more sensor 50, as described above, or may connect to one or more sensor of a handheld computing device 30 in order to determine its position within the environment. For instance, a user may point at a television 101 and turn the television on or off even without the visual device 26 to depict a status 105 of the television 101. Thus, one may appreciate that the electro-tactile stimulator 28 may include a wide variety of sensors 50 and the visual device 26 may include a wide variety of sensors 27. Sensors 50 and sensors 27 may include accelerometers, gyroscopes, global positioning satellite (GPS) components, compasses, Light Detection and Ranging (LIDAR) components, sonar, radar, and/or the like. Moreover, a separate illuminator device (not shown) may be utilized to paint a constellation or pattern on an environment, including a pattern of light invisible to a human, which may be sensed by sensor 50 or sensor 27 to ascertain spatial information regarding a location, such as a location of an electro-tactile stimulator 28 in an environment.

Thus, a sensory augmentation platform 20 may sense a user's surrounding environment, create a 3D model of an environment, and permit interaction with the model via electro-tactile stimulators 28. The model may be shared with other users and may be projected or presented on other visual devices 26 so that other users may, utilizing their own electro-tactile stimulators 28, remotely interact with the model. Furthermore, a user may generate a unique user profile, so that the motion of the user and the user's electro-tactile stimulators 28 maybe specifically, accurately, and precisely tailored to the biology and personal attributes of the user. For instance, a user may move one's finger having an electro-tactile stimulator 28 through a full range of user arm motion to plot the extreme boundaries of potential motion. Such motion may be plotted relative to a location of a visual device 26 which may be worn on the user's head. In this manner, both the visual device 26 and the electro-tactile stimulator 28 may be calibrated for use by a specific user, and such calibration stored in a unique user profile.

While a computing device 30 has been discussed, as has an augmentation control server 34, in various instances, one or more additional computing device 30 may be provided, called a local network node (not shown). The local network node may comprise a location specific processing module reposed within a specific physical site. In further instances, the local network node may be a logical instance running remotely within an augmentation control server 34 and accessible such as by a network. The local network node may be associated with a location, a user, an account and/or a combination thereof. In various embodiments, access to the local network node requires recurring subscription payments. In various instances, the 3D model of the environment may be processed and/or stored in the local network node. In this manner, processor and memory load on electro-tactile stimulators 28 and visual devices 26 may be ameliorated.

Moreover, the local network node may be implemented to facilitate additional features of a 3D model of an environment. For instance, a user may create a home area, map the home area, assign locations to controllable devices in the home area, and automatically gain access to control the controllable devices upon entry into the home area. For instance, a local network node may be associated with a living room and may facilitate control of a television by pointing with an electro-tactile stimulator 28 in the direction of the television. Similarly, a local network node may facilitate control of an "virtual white board" whereby a user may draw in space on a blank wall of a room, or may load textures onto surfaces, the drawings and textures stored and at runtime, rendered, by the local network node.

In yet further use cases, a store may implement a local network node. A store may map products and store this mapping in a local network node, such as by walking about the room with a visual device 26 and/or with electro-tactile stimulators 28. Subsequently, a customer may enter the store and make purchases by picking up an article, permitting the visual device 26 and/or electro-tactile stimulator 28 to determine the selection of the object in connection with a local network node, and may facilitate purchasing of the item by an interaction with an electro-tactile stimulator 28. Thus, one may appreciate that a local network node may be locked to one or more user, or may permit connection by new users, such as customers, who enter a geographic region associated with the perimeter of a store.

Yet furthermore, a local network node may facilitate prompt alerting of police, fire, rescue services, and other resources as desired. For example, a local network node may facilitate calling the police in connection with detecting a pattern of user behavior by visual devices 26 or electro-tactile stimulators 28 corresponding to a fall by a specific elderly user, but not when the fall corresponds to a user who is a gymnast. Alternatively, the local network node may facilitate calling the police in connection with detecting a pattern of user behavior by visual devices 26 and/or electro-tactile stimulators 28 of any user corresponding to a fall and then a particular elapsed delay in arising from the fall, or in connection with pointing and/or gesturing by the user at a specific panic button or the like.

Yet furthermore, additional plugin services may be implemented, whether on an as-needed basis, or a subscription basis. For instances, a user may activate a GPS mapping plugin automatically upon connection to a local network node associated with an automobile, thereby facilitating provision of turn-by-turn instructions through electro-tactile stimulation or visual indication upon entry into the vehicle, while not burdening the electro-tactile stimulator 28 or the visual device 26 with the memory and computational loads associated with GPS mapping when not in the vehicle.

In various embodiments, the local network node may be termed a "hub." A hub, may, in various embodiments, provide a fixed point that a user may create, such as through an application on an electronic device, and may be located in or associated with a context environment. The hub may marshal data and facilitate efficient generation of user experiences. While the hub is discussed as a physical device located at a context environment, one may also appreciate that the hub may be a cloud-based data collection that is electronically associated with the context environment but not necessarily co-located therewith. In at least some examples, the local network node (or hub) may be, may be a component of, may be co-housed with, or may otherwise share at least some computing resources with, the augmentation control server 34 and/or the smart home hub 102, described above herein.

In various embodiments, the hub is a network node localized to a context environment. A hub may receive, process, and output a variety of types of data. For instance, the hub may receive sensory data from sensors. In further instances, the hub may receive data from third party sources, for example information from the internet. The hub may receive connections from IoT devices, and the IoT devices may provide data to the hub and/or receive data from the hub. While in various instances the hub may receive, process, and transmit data to wearable devices of a user for sensory augmentation, in further instances, any type of data may be received, processed, and transmitted to any electronic device. Moreover, the hub may interact directly with a user, such as via human readable outputs directly on the hub. In various embodiments, the hub receives data, creates 3D models for display in connection with augmented reality experiences, may track a location of a user in real-time (such as via sensors), may change and update the 3D models at least partially in response to the tracking the location of the user, and may generate output data for provision to the user and/or electronic devices (such as wearable electronics) of the user. The hub may also generate output data for provision to third parties and/or third-party electronic devices.

Figure 10:
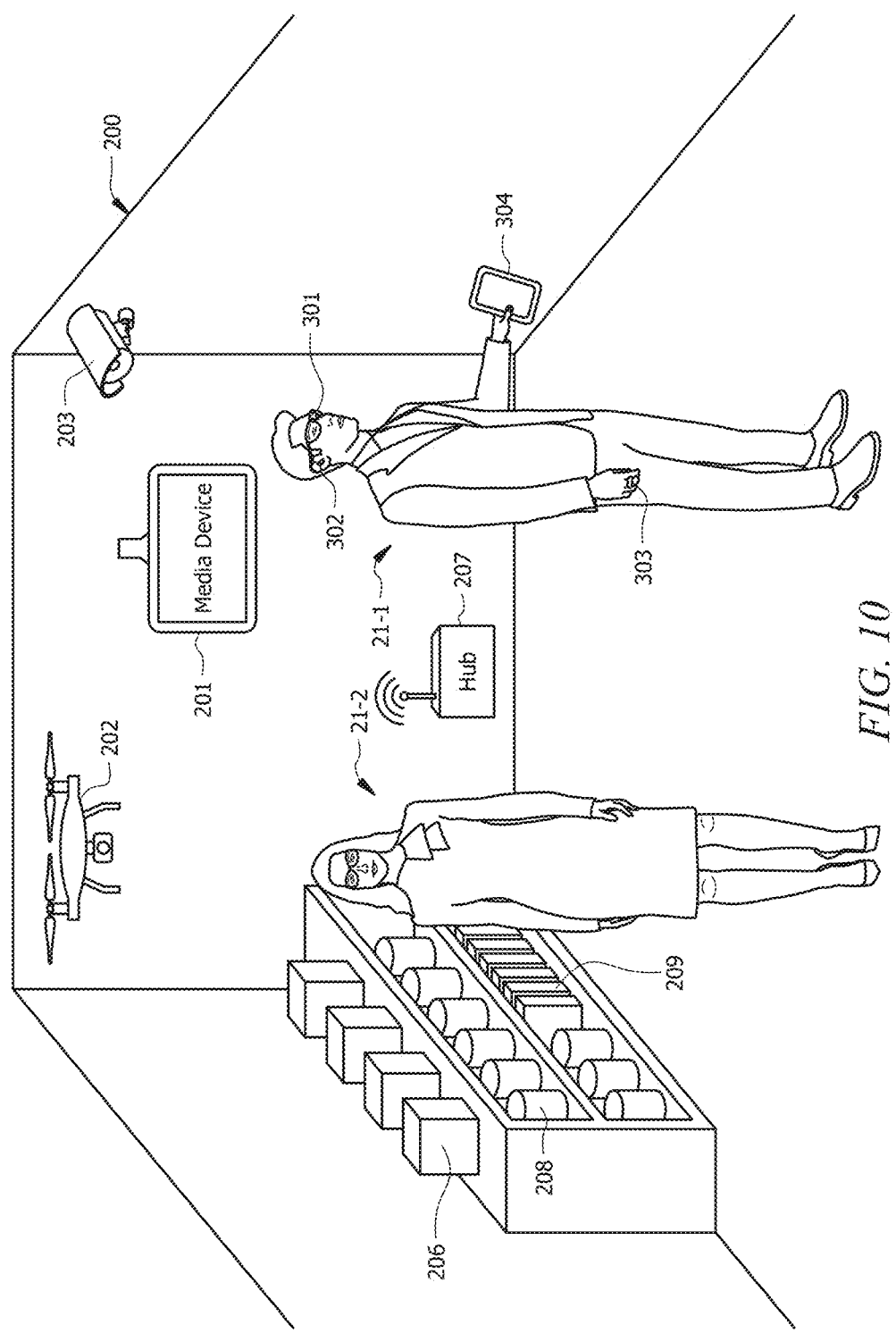
FIG. 10 is an example context environment with a hub device in accordance with aspects of the disclosure.

With reference to FIG. 10, a hub 207 may be located at, or otherwise associated with, a context environment, such as context environment 200. In at least some examples, the hub 207 may be, may be a component of, may be co-housed with, or may otherwise share at least some computing resources with, the augmentation control server 34 and/or the smart home hub 102. A context environment may comprise any data, such as human sensible data. For example, the context environment may include human sensible aspects such as location, sight, sound, touch, sensation, taste, smell, temperature, and/or the like, that is associated with a particular location or experience. A context environment may include other types of data, such as payment information, machine readable aspects, such as information that the hub provides to/from other electronic devices or sensors. For instance, a store might be a context environment, or a home, or a specific circumstance, such as a sales transaction within a store. Thus, the context environment may be a combination of spatial, temporal, sensory, and electronically detectable content, all linked in a common relation, such as by location, time, common purpose, common human participant(s), common machine participant(s), and/or the like. A context environment may comprise a collection of points such as a point cloud mapped in an augmented reality cloud accessible by the system.

FIG. 10 shows one example context environment 200. With reference to both FIGS. 10 and 2, a first user having a first sensory augmentation system 21-1 and a second user having a second sensory augmentation system 21-2 are co-located within a common location, thus being in a same context environment 200. The first sensory augmentation system 21-1 may include machine-human interface features such as smart glasses 301 which may contain a visual device 26 (not shown), audio earpiece 302, finger device 303 which may contain, or be, an elector-tactile stimulator 28 (not shown), a smartphone 304 having, or implemented as, a handheld computing device 30 (not shown). The context environment 200 may include fixed sensors 203, such as a camera, portable sensors, such as a camera-carrying drone 202, media devices 201, such as a television display, merchandise for purchase 206, 208, 209, and/or the like. Each of these items may provide data to the hub 207, the locations thereof may be mapped by the hub 207, and/or may receive data from the hub 207. As such, the hub 207 may have data associated with the context environment 200 and one or more components of the context environment 200.

Users may travel from one context environment 200 to another. For example, with reference to FIGS. 11 and 2, a network 32 connects multiple hub devices, such as a first hub 207-1 associated with a first context environment 200-1, a second hub 207-2 associated with a second context environment 200-2, and a third hub 207-3 associated with a third context environment 200-3. Each context environment 200-1, 200-2, 200-3, may have an associated hub device. For example, first context environment 200-1 may have a first hub 207-1, a second context environment 200-2 may have a second hub 207-2, and a third context environment 200-3 may have a third hub 207-3. Moreover, each context environment 200-1, 200-2, 200-3, may have an associated augmented reality point cloud. For example, first context environment 200-1 may have a first augmented reality point cloud 210-1, a second context environment 200-2 may have a second augmented reality point cloud 210-2, and a third context environment 200-3 may have a third augmented reality point cloud 210-3. Each augmented reality point cloud may be a data store within the relevant hub that captures the data associated with the context environment. Thus, an augmented reality point cloud may be an electronic map of the context environment, stored in the hub or stored in association with the hub.

The sensory augmentation system of each user, as well as the hubs of each context environment may be connected by a network 32. Thus, as a user moves from one context environment to another, the sensory augmentation system of that user may connect with a different hub. For example, a first user may have a first sensory augmentation system 21-1, a second user may have a second sensory augmentation system 21-2, and a third user may have a third sensory augmentation system 21-3. As users moves about among context environments, one or more of the sensory augmentation systems may connect to or otherwise interact with one or more hub and the corresponding augmented reality cloud(s).

Figure 11:
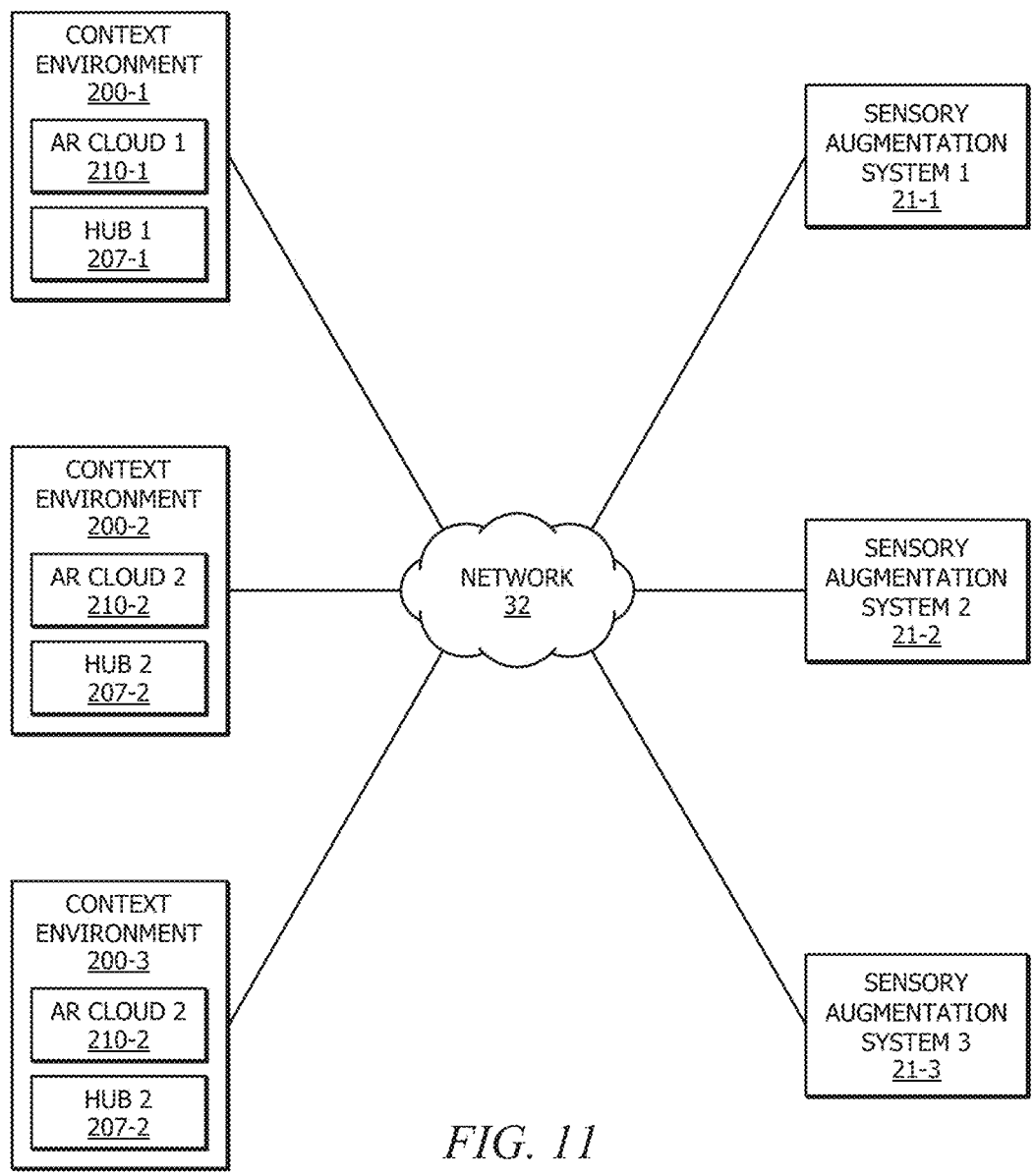
FIG. 11 is a diagram showing example relationships among multiple sensory augmentation systems and multiple context environments in accordance with aspects of the disclosure.
Figure 12:
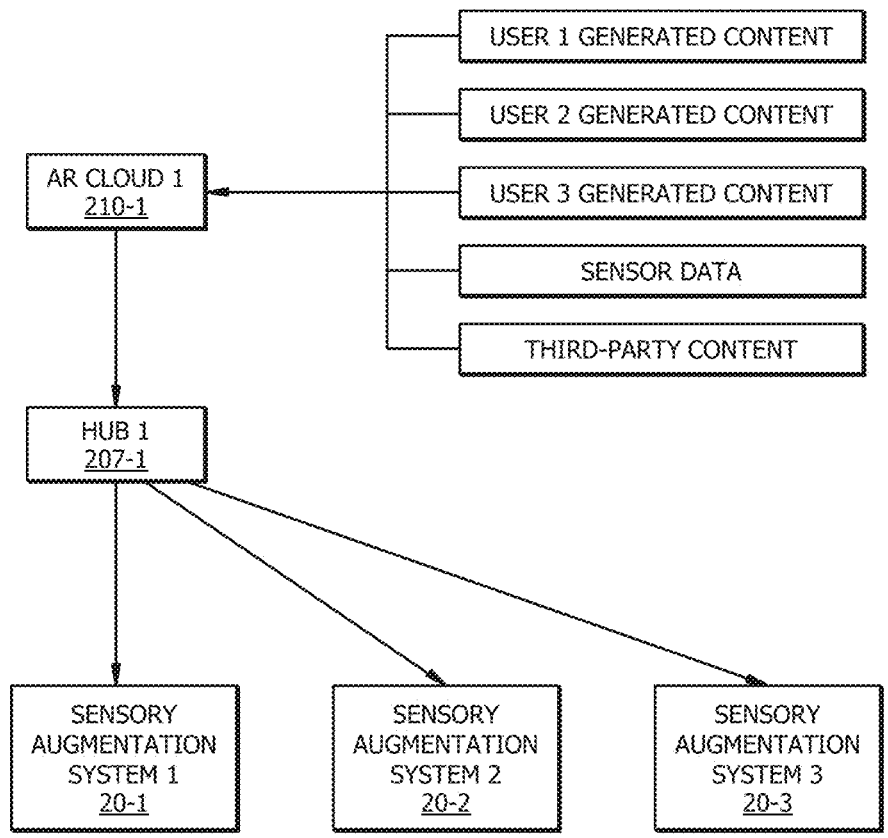
FIG. 12 is a diagram showing example relationships among data associated with a context environment and multiple sensory augmentation systems in accordance with aspects of the disclosure.

Referring now to FIG. 12, as well as FIGS. 2 and 10-11, because a context environment has diverse data from many sources, different aspects of the augmented reality point cloud, and/or other data, may have different permissions. Thus, different users may have interest in and/or authorization for different data. For example, a first context environment 200 may include data generated by a first user's first sensory augmentation system 21-1, as well as data generated by other sensory augmentation systems—such as a second user's second sensory augmentation system 21-2, a third user's third sensory augmentation system 21-3, etc. The first context environment 200 may have sensor data from sensors such as sensors 203 and 202 (FIG. 10). The first context environment 200 may include third-party content from other sources, such as external network sources, the internet, etc., as well as any other user content, such as manually generated user content that is uploaded to a hub. The first hub 207-1 may permit different users to access different portions of this data. For example, different portions may be provided to the first sensory augmentation system 21-1, second sensory augmentation system 21-2, and third sensory augmentation system 21-3. Thus, it may be said that the hub device generates a custom augmented reality point cloud corresponding to each user, from the stored augmented reality cloud associated with that hub.

Figure 13:
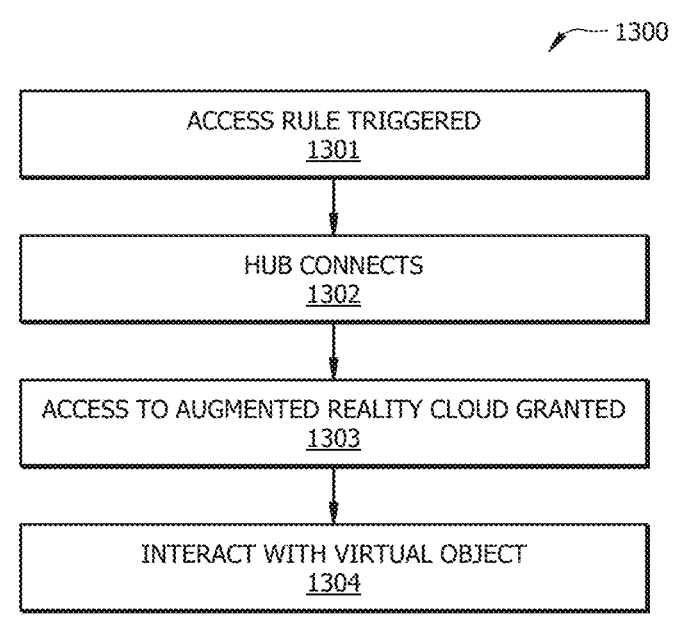
FIG. 13 is flowchart of an example method of user interaction with a context environment in accordance with aspects of the disclosure.

FIG. 13 is a flowchart of a method 1300 of user interaction with a context environment. In at least some examples, the method 1300 may be implemented in various parts by the sensory augmentation platform 20, the sensory augmentation system 21, and/or the augmentation control server 34. Referring to FIGS. 2, 10-12, and 13, the method 1300 may begin with a user sensory augmentation system, such as a sensory augmentation system 21, triggering a context environment access rule (block 1301). For example, an aspect of the user's sensory augmentation system may detect entry into a context environment. For instance, an aspect of the sensory augmentation system 21 may connect to or detect a presence of the first hub 207-1, or passage across a geofence, or detection of a scanned quick response (QR) code, or visual identification of a sign or other item within the context environment. The hub that is associated with the context environment may connect to the sensory augmentation system of the user (block 1302). Thus, the voluminous data associated with the augmented reality point cloud may be accessed by the user's sensory augmentation system. By reposing this data and/or processor load with the hub, rather than the user's sensory augmentation system, processor load and power consumption may be optimized and enhanced. Thus, access to the augmented reality cloud may be granted by the hub to the user's sensory augmentation system (block 1303). Subsequently, the user may utilize the user's sensory augmentation system to interact with virtual items stored in the augmented reality cloud of the hub associated with the context environment (block 1304).

Having discussed architectural aspects of a context environment, system, and hub, further aspects are now discussed. Although specific reference may not be made to below to individual figures, the following discussion is application to any one or more of the figures of this disclosure. A user may interact with the context environment, system, and hub, and may further select plugins comprising operative code and data that can interact with the augmented reality cloud and associated data. For instance, a user may create a plugin that feeds data to the augmented reality cloud. A user may create his or her own virtual objects within the augmented reality cloud. In some examples, the user may provide the virtual objects for distribution to other users. In at least some examples, the user may receive compensation in return for such distribution. In various embodiments, a variety of plugins are contemplated to facilitate enhanced user experiences. For example, a plugin to facilitate creation of 3D virtual objects is possible. A user may customize 3D objects, interact with 3D objects, etc. In further instances, a plugin to facilitate creation of infrastructure within a context environment, is implemented. A user may use sensors, such as a camera and application running on a smartphone, in order to generate a model of a room, building, area, or other context environment, and upload this model to the hub for inclusion into the augmented reality point cloud. Model creation may also proceed automatically, such as through the accumulation of data from sensors and application of machine learning.

Moreover, residential and commercial use cases for the plugins may be provided. For example, a user may arrive at a context environment comprising a user's home, and using a software application on a personal electronic device, access a home screen. On such screen a user may receive suggestions of relevant plugins. A user may point at or otherwise interact with virtual objects such as recipes hovering in smart glasses near a stove, videos hovering in smart glasses on an empty wall, home security system notifications delivered silently by electro-tactile stimulation, and/or the like.

In further instances, a commercial use case may include many users going to a restaurant and connecting to a hub associated with the context environment comprising the restaurant. The hub may provide users with a plugin to view a menu board on smart glasses, and may provide a store manager with a plugin to access demographic, financial, and other data associated with store performance and users visiting the store and connecting to the hub.

Many different plugins are contemplated. For example, a user preferences plugin may allow a user to define personally identifiable data, set sharing preferences for data, establish a virtual object representing the user, and/or the like. A plugin marketplace may facilitate acquisition of new plugins. A wallet plugin may facilitate the establishment of payment information to permit transactions via the augmented reality environment. An artificial intelligence plugin may provide notifications and recommendations to users based on rules, heuristics, and/or machine learning. A health plugin may provide for data and health monitoring aspects. An electro-tactile stimulator plugin may facilitate control of electro tactile stimulators, training of a user to use an electro-tactile stimulator, and/or the like. A hub control plugin may facilitate control of the hub device and interfacing of the hub device with third party systems, such as security systems, point of sale systems, remote controls and/or the like.

Figure 14:
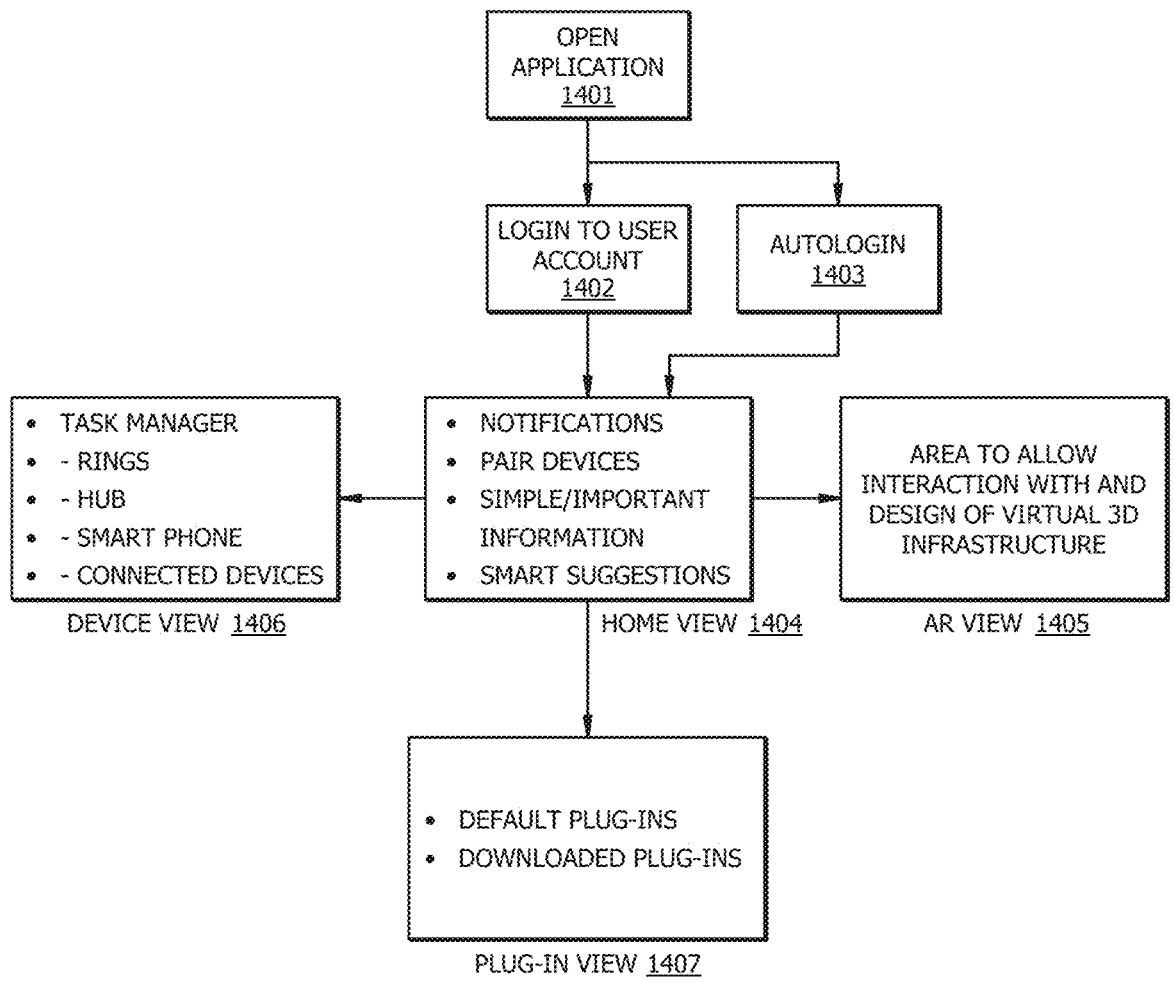
FIG. 14 is a diagram showing example aspects of a user interface workflow in accordance with aspects of the disclosure.

With reference now to FIG. 14, an example diagram of a user interface workflow 1400 for a user interacting with an application to control a hub (e.g., such as the augmentation control server 34 or the local network node) and/or system (e.g., such as the sensory augmentation system 21 or sensory augmentation platform 20) is shown. A user may utilize an electronic device (e.g., such as the computing device 30) with a software application to access the system. The user may open the application (block 1401). The user may log in to a user-specific account (block 1402), or may be automatically logged in (block 1403) such as in response to biometric data collected by a sensor such as on an electro-tactile stimulator, and/or the like. A user interface may be displayed, such as on a screen, or smart glasses, or a smartphone. The user interface may include multiple views. For example, a home view (block 1404) may facilitate interaction with notifications, the establishment of connections with devices ("pair devices"), simple and/or important information, and smart suggestions, such as recommended plugins to install. An augmented reality (AR) view (block 1405) may be an area designed to allow a user to interact with and/or design virtual 3D infrastructure, such as to create and map a virtual environment onto a context environment such as a room, through the user of sensors such as smartphone cameras, and/or the like. A plugin view (block 1407) may facilitate interaction with and acquisition of plugins, including default and downloaded plugins. A device view (block 1406) may facilitate control and setup of aspects of the system, such as electro-tactile stimulations (e.g., via rings, such as the electro-tactile stimulator 28), the hub, a smartphone, and/or other connected devices.

Having discussed aspects of a system and method provided herein, general features relevant to electronic communication are further outlined below. As used herein, the term "network," such as with respect to a network which may comprise at least a portion of network 32 provided in FIG. 2, includes any cloud, cloud computing system or electronic communications system or method which incorporates hardware and/or software components. Communication among the parties may be accomplished through any suitable communication channels, such as, for example, a telephone network, an extranet, an intranet, Internet, hotspot, online communications, satellite communications, offline communications, wireless communications, transponder communications, local area network (LAN), wide area network (WAN), virtual private network (VPN), networked or linked devices, keyboard, mouse and/or any suitable communication or data input modality. For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In at least some examples, the augmentation control server 34, the smart home hub 102, and/or the local network node described above herein may be a spatial computing device that is spatially and situationally aware of other computing or electronic devices located proximate to the spatial computing device. The spatial computing device, in some examples, receives data representing an environment in which the spatial computing device is located. The data may be an output of a simultaneous localization and mapping (SLAM) process, such as generated by a SLAM capable device. In at least some examples, the computing device 30 may be a SLAM capable device. The SLAM capable device may be a smartphone, tablet, or other device having LIDAR functionality, radar functionality, a camera, or any other sensors or components that enamel the SLAM capable device of generating data representative of a 3D space. Such data capture may be performed according to any suitable means for 3D spatial data capture, the scope of which is not limited herein. The data may form, or based on the data the spatial computing device may generate, a 3D spatial map of the environment in which the spatial computing device is located and which has been scanned or otherwise processed by the SLAM capable device to generate the data. The 3D spatial map is, in at least some examples, a map of a space that was scanned by the SLAM capable device, such as a room of a home, multiple rooms of a home, areas of a retail environment, etc.

After receiving the spatial map, the spatial computing device computes spatial data for the environment, establishing itself as a point of origin in the spatial map. For example, the spatial computing device utilizes ultra-wideband, Bluetooth®, and/or wireless radio wave technologies to localize electronic devices (such as Internet-enabled, Internet of Things devices, or any device that can send or receive a wireless signal and/or is capable of electronically communicating with the spatial computing device) within the environment and position them within the spatial map. For example, the electronic devices may be localized in the environment based on signal processing including Time of Flight, Time of Arrival, Fine Time Measurement, wireless signal triangulation including the electronic device, the spatial computing device, and at least one other device, etc. The electronic devices are located in the spatial map relative to the point of origin (e.g., the spatial computing device) and are tracked substantially continuously to maintain accurate spatial data for the environment. In this way, the spatial computing device maintains a spatial and situational awareness of the environment and the electronic devices within the environment.

In some examples, the spatial computing device receives the data from the SLAM capable device and generates the spatial map in substantially real-time. Further, in at least some examples the spatial computing device localizes at least some of the electronic devices in the spatial map in substantially real time-time, tracking and rendering an avatar or other indicator corresponding to the electronic devices in the spatial map as the electronic devices move in the area represented by the spatial map.

The spatial map is viewable, in some examples, in a bird's eye view perspective such that the position and orientation of the electronic devices within the environment is viewable. The spatial map is viewable through a web user interface for a user located remotely, through a monitor communicatively coupled to the spatial computing device, on a display of a smartphone or tablet in communication with the spatial computing device, etc. Further, the spatial map is editable via a graphical interface hosted or presented by the spatial computing device, or a graphical interface of another device that communicates with the spatial computing device (e.g., such as a smartphone or other computing device, a web-based user interface that access data of the spatial computing device), etc. For example, the spatial map is editable to reposition data points provided by the SLAM capable device, correct or modify localized positions of the electronic devices in the environment, place digital elements within the environment, etc.

In at least some examples, based on the spatial awareness of the spatial computing device, the spatial computing device alone, or in combination with one or more spatial computing devices located in other environments, facilitate user interaction's such as via shared spaces or a live view in which a user views an augmented reality (AR) layer of the spatial data maintained by the spatial computing device. For example, viewing the environment through an electronic device having been localized in the environment by the spatial computing device, a user may view AR elements in the environment. For example, the spatial computing device, in conjunction with another spatial computing device in another environment, may each identify shared spaces or zones within their respective environments. The shared spaces may be shared between users of the respective spatial computing devices such that, when viewed through a screen of a device communicatively coupled to one of the respective spatial computing devices, digital elements placed within the share spaces are visible to each of the users. Two respective spatial computing devices in two different environments may each identify a shared space for sharing between two users.

The users may place a digital game board within the shared space such that the digital game board is viewable to each of the users when the shared space is viewed by one of the users through a screen of a device communicatively coupled to one of the respective spatial computing devices. The users may have user input devices for interacting with the shared space, the scope of which are not limited herein, that enable the users to move pieces on the digital game board. The spatial computing devices communicate these moves so that each user views an up to date or current version of the digital game board when the shared space is viewed through a screen of a device communicatively coupled to one of the respective spatial computing devices. In at least some examples, movement of a digital piece on the digital game board is trackable and determinable by the spatial computing device based on movement of an IoT or user input device. In some examples, the tracking and determination of movement is performed by the spatial computing device triangulating a position of the IoT or user input device, such as may be worn on a user's hands. In some examples, the user input device is the electro-tactile stimulator 28, as described elsewhere herein. In other examples, the user input device is a ring as described in U.S. patent application Ser. No. 16/944,506, filed on Jul. 31, 2020 and titled "Smart Ring," which is incorporated herein by reference in its entirety.

In some examples, the spatial computing device operates as a shared server that shares the spatial map and spatial data maintained by the spatial computing device with devices communicatively coupled to the spatial computing device. These devices may be, or may not be, devices within the environment of the spatial computing device and/or which have been, or are being, localized by the spatial computing device. For example, the spatial computing device may be located in a retail environment and may be maintaining special awareness of electronic devices and/or digital elements within the retail environment. A user may access the spatial data maintained by the spatial computing device to digitally explore the retail environment and/or interact with at least some digital elements (including artificial reality elements) within the retail environment. The user may also be located in the retail environment or may be located outside the retail environment (e.g., across the hall from the retail environment, across the street from the retail environment, etc.) and communicatively coupled to the spatial computing device.

Additionally, in some examples a user may choose to share demographic or other information with a spatial computing device. For example, the user may configure sharing settings on the user's electronic device. When the user's electronic device communicatively couples to the spatial computing device, either to remotely view and/or interact with spatial data maintained by the spatial computing device or to register with the spatial computing devices, such as to be localized within a spatial map, information may be transferred from the user's electronic device to the spatial computing device. In this way, the spatial computing device may learn, such as according to machine learning or other artificial intelligence processes, correlations between the user based on the user's shared information and actions of the user as observed by the spatial computing device. These observed actions could be, for example, a user viewing but not entering an environment for which the spatial computing device maintains spatial data, actions taken while being localized within a spatial map by the spatial computing device, etc.

At least some implementations of the spatial computing device include additional functionality. For example, the spatial computing device may also operate as a home server, a cloud computing device, etc. The spatial computing device may host and deliver media content, unrelated to the spatial data maintained by the spatial computing device, to a device coupled to the spatial computing device. The spatial computing device, either as a part of, or independent from, the spatial data maintained by the spatial computing device, may couple to a plurality of control and/or display devices to operate as a gaming center or gaming console for playing electronic games. The spatial computing device, either as a part of, or independent from, the spatial data maintained by the spatial computing device, may facilitate off-loading of certain operations or functions from user devices communicatively coupled to the spatial computing to facilitate increased performance related to those operations or functions.

In at least some examples, the spatial map and other spatial data maintained by the spatial computing device may be shared with other components that enter the environment for which the spatial computing device maintains the spatial data. For example, some home automation or assistance devices (e.g., such as robotic devices) may generate maps of an environment to enable their operation. In one example, a robotic vacuum generates a map of floor space by moving in s straight line until it strikes an object and then changes direction. By repeating this action over and over again, the robotic vacuum develops a map and awareness of an environment in which it is operating. However, this process is highly inefficient, consuming unnecessary time and energy. At least some such robotic devices may be operable with the spatial computing device in a plug and play manner such that upon entering the environment and communicatively coupling to the spatial computing device, the robotic device receives, or receives access to, the spatial map maintained by the spatial computing device. In other examples, the spatial computing device provides the vacuum or other robotic device with a defined path to follow, providing navigation instructions to the vacuum or other robotic device. In this way, the spatial computing device can either provide (e.g., supplant pre-existing or provide in the first instance) navigation information to the vacuum or other robotic device, or augment existing navigation information of the vacuum or other robotic device, increasing efficiency of operation of these robotic devices.

Figure 15:
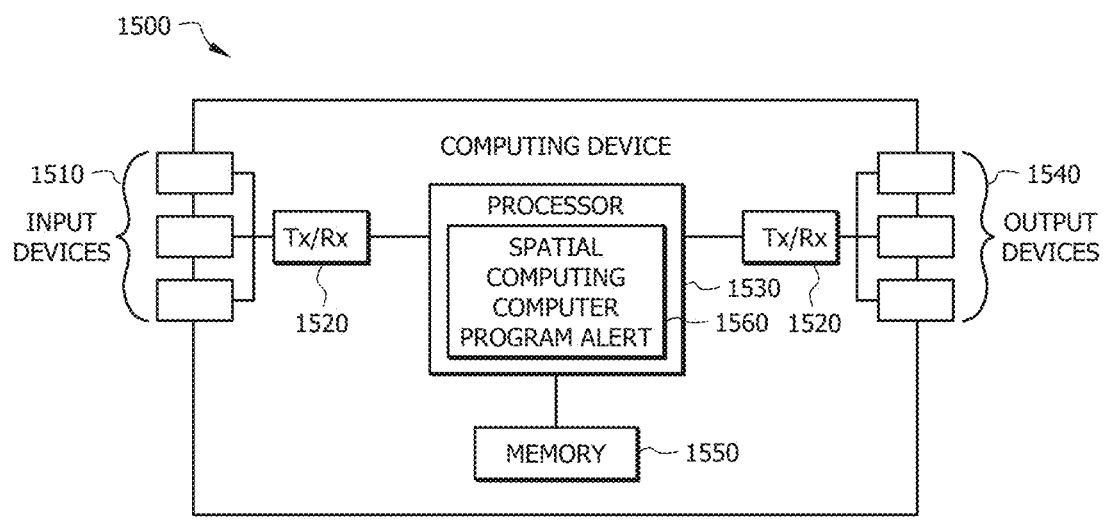
FIG. 15 is a block diagram of an example computing device in accordance with aspects of the disclosure.

Referring now to FIG. 15, a block diagram of an example computing device 1500 is shown. Computing device 1500 is any suitable processing device capable of performing the functions disclosed herein such as a processing device, a user equipment, an Internet of Things (IoT) device, a computer system, a server, a computing resource, a cloud-computing node, a cognitive computing system, etc. In at least some examples, the computing device 1500 is suitable for implementation as a spatial computing device, as described herein. Computing device 1500 is configured to implement at least some of the features disclosed herein, for example, the spatially aware computing described herein. In various embodiments, for instance, the features of this disclosure are implemented using hardware, firmware, and/or software (e.g., such as software modules) installed to run on hardware. In some embodiments, the software utilizes one or more software development kits (SDKs) or SDK functions to perform at least some of the features/methods of this disclosure.

In some examples, the computing device 1500 is an all-in-one device that performs each of the aforementioned operations of the present disclosure, or the computing device 1500 is a node that performs any one or more, or portion of one or more, of the aforementioned operations. In one embodiment, the computing device 1500 is an apparatus and/or system configured to implement a spatially aware computing environment, according to a computer program product executed on, or by, at least one processor. In various examples, the computing device 1500 may be suitable for implementation as the augmentation control server 34, as the smart home hub 102, and/or as the local network node, each as described above herein, or as any other computing device of this disclosure.

The computing device 1500 comprises one or more input devices 1510. Some of the input devices 1510 include at least some of cameras, magnetic sensors, temperature sensors, pressure sensors, accelerometers, microphones, keyboards, touchscreens, buttons, toggle switches, and/or other devices that allow a user to interact with, and/or provide input actively or passively to, the computing device 1500. Some other of the input devices 1510 are downstream ports coupled to a transceiver (Tx/Rx) 1520, which are transmitters, receivers, or combinations thereof. The Tx/Rx 1520 transmits and/or receives data to and/or from other computing or electronic devices via at least some of the input devices 1510. Similarly, the computing device 1500 comprises a plurality of output devices 1540. Some of the output devices 1540 include at least some of speakers, a display screen (which, in some examples, is also an input device such as a touchscreen), lights, or any other device that allows a user to interact with, and receive output from, the computing device 1500. At least some of the output devices 1540 are upstream ports coupled to another Tx/Rx 1520, wherein the Tx/Rx 1520 transmits and/or receives data from other nodes via the upstream ports. The downstream ports and/or the upstream ports include electrical and/or optical transmitting and/or receiving components. In another embodiment, the computing device 1500 comprises one or more antennas (not shown) coupled to the Tx/Rx 1520. In at least some examples, the antennas facilitate the localization of electronic devices proximate to the computing device 1500, such as via ultra-wideband, Bluetooth®, or other radio wave technologies using techniques as discussed above. The Tx/Rx 1520 transmits and/or receives data from other computing or storage devices wirelessly via the one or more antennas. In yet other embodiments, the computing device 1500 includes additional Tx/Rx 1520 such that the computing device 1500 has multiple networking or communication interfaces, for example, such that the computing device 1500 communicates with a first device using a first communication interface (e.g., such as via the Internet) and communicates with a second device using a second communication interface (e.g., such as another computing device 1500 without using the Internet).

A processor 1530 is coupled to the Tx/Rx 1520 and at least some of the input devices 1510 and/or output devices 1540 and is configured to implement the spatial computing environment. In an embodiment, the processor 1530 comprises one or more multi-core processors and/or memory modules 1550, which functions as data stores, buffers, etc. The processor 1530 is implemented as a general processor or as part of one or more application specific integrated circuits (ASICs), field-programmable gate arrays (FPGAs), and/or digital signal processors (DSPs). Although illustrated as a single processor, the processor 1530 is not so limited and alternatively comprises multiple processors. The processor 1530 further comprises processing logic configured to execute a spatial computing computer program product 1560 that is configured to perform spatial computing and/or implement the spatial computing environment described herein.

FIG. 15 also illustrates that a memory module 1550 is coupled to the processor 1530 and is a non-transitory medium configured to store various types of data. Memory module 1550 comprises memory devices including secondary storage, read-only memory (ROM), and random-access memory (RAM). The secondary storage is typically comprised of one or more disk drives, optical drives, solid-state drives (SSDs), and/or tape drives and is used for non-volatile storage of data and as an over-flow storage device if the RAM is not large enough to hold all working data. The secondary storage is used to store programs that are loaded into the RAM when such programs are selected for execution. The ROM is used to store instructions and perhaps data that are read during program execution. The ROM is a non-volatile memory device that typically has a small memory capacity relative to the larger memory capacity of the secondary storage. The RAM is used to store volatile data and perhaps to store instructions. Access to both the ROM and RAM is typically faster than to the secondary storage.

The memory module 1550 houses the instructions for carrying out the various embodiments described herein. For example, the memory module 1550 comprises the spatial computing computer program product 1560, which is executed by processor 1530.

In other examples, the computing device 1500 is suitable for implementation as an electronic device (such as the computing device 30) that is adapted to communicatively couple to the spatial computing hub described herein, or to operate independently of the spatial computing device described herein but still perform spatial computing actions. In such an example, the spatial computing computer program product 1560 may be an application configured to operate on the electronic device. The application may have multiple functions, including at least scanning, an ability to interact with a marketplace hosted remotely from the computing device 1500 (e.g., such as on a spatial computing device and/or in the cloud), a live view function, and a create tool.

The scanning function may enable the computing device 1500 to scan and obtain data to represent a 3D space (e.g., a room) as a 3D spatial map, as described elsewhere herein. In some examples, the spatial map is provided to a spatial computing device, as described elsewhere herein. In other examples, the spatial map, or a portion of the spatial map, is retained on the electronic device. The spatial map may be generated according to any suitable means, including at least LIDAR or machine learning based on a camera sensor output.

The create function, in at least some examples, allows a user to create digital assets or elements for use in the spatial map. The digital assets may be 3D or two-dimensional (2D). Various examples of digital assets include skins or textures that may be applied to various planes or surfaces present in the spatial map, objects, experiences (e.g., interactive and/or animated content, content that has a progression such as a game, etc.) or other assets that can interface with or otherwise be inserted into or applied to at least a portion of the spatial map. Digital assets created by the create tool may be saved to an archive or repository on the electronic device, such as an asset backpack. In at least some examples, the digital assets may be implemented as plugins as described elsewhere herein.

The live view function, in at least some examples, enables a user to view the spatial map, either stored locally on the electronic device or remotely, such as on a spatial computing device as described elsewhere herein. The user may also manipulate the spatial map via the live view function, such as by inserting digital content or assets from the asset backpack into the spatial map, modifying the spatial map, etc. Further, the user may tag or otherwise define regions of the spatial map based on real-world objects that are present in the location (e.g., such as a television) such that by viewing this tagged location via the live view function, a user may provide commands to or otherwise interact with a real-world element present at that location. In at least some examples, when the live view function is activated, the electronic device performs scanning to determine a location of the electronic device within the spatial map and/or to update, or create a portion of, the spatial map.

The application is, in some examples, operable to communicate with an online marketplace. The user may purchase digital assets (such as the textures, objects, experiences, games, etc.) described above from the marketplace. The user may also provide content created via the create tool and stored in the asset backpack to the marketplace for sale. Transactions occurring on the marketplace may occur in a virtual currency unique to the spatial computing environment or may occur via electronic forms of monetary currency. In some examples, monetary currency and the virtual currency unique to the spatial computing environment may be interchanged (e.g., virtual currency unique to the spatial computing environment may be exchanged for monetary currency that is withdrawn and monetary currency may be deposited and exchanged for the virtual currency unique to the spatial computing environment).

In some examples, via the live view function a user may interact with the spatial map to take part in an experience or play a game. For example, the live view function may enable digital elements to be placed in the spatial map and the user may view the spatial map through a display of the electronic device. Based on this viewing, the user may interact with the digital elements to play a game, such as by finding the digital elements, popping or mining the digital elements, etc. In some examples, performing a task, achieving a goal, winning a game, etc. may award currency usable or exchangeable in the marketplace and/or other digital assets that may be saved to the asset backpack.

In at least some further examples, the live view may enable a user to purchase real-world objects. For example, when communicatively coupled to a spatial computing device as described herein, the spatial computing device may host and maintain the spatial map displayed by the electronic device via the live view. In this example, the spatial computing device may define, or have an awareness of, a location of certain real-world objects (e.g., such as in a store, as described above with respect to FIG. 10). By localizing the electronic device in the spatial map, if a user of the electronic device points the electronic device at the real-world object and selects a purchase option, a transaction may be performed. Because the spatial computing device has spatial awareness of the real-world object, and has localized the electronic device and therefore knows a location and viewpoint orientation of the electronic device with respect to the real-world object, the spatial computing device is able to determine that the user wishes to purchase the real-world object without requiring a barcode or other unique identifier of the real-world object to be scanned.

In yet other examples, the application, as an element of the live view function or independent of the live view function, enables a shared space interaction. The shared space interaction enables two or more users located remotely from one another to interact with digital assets that appear in the shared space. In at least some examples, each user taking part in the shared space experience views the same digital assets within the shared space. For example, the users may interact with each other to play a game (e.g., a number of digital balloons may be presented in the shared space and multiple users may view the balloons and attempt to pop the balloons, where a player who pops the most balloons in the shared space is the winner). The user may take part in the game partially within the shared space (e.g. to receive instructions common to all players), exit the shared space for a portion of the game (e.g. such as to search for objects), and then may again return to the shared space (e.g., such as to show or turn in the found object(s)). These and other functions application to spatial computing and spatial computing actions may be performed by, or via, the application.

It is understood that by programming and/or loading executable instructions onto the computing device 1500, at least one of the processor 1530 and/or the memory module 1550 are changed, transforming the computing device 1500 in part into a particular machine or apparatus, for example, a spatial computing system for implementing a spatial computing environment having the novel functionality taught by the present disclosure. It is fundamental to the electrical engineering and software engineering arts that functionality that can be implemented by loading executable software into a computer can be converted to a hardware implementation by well-known design rules known in the art. Decisions between implementing a concept in software versus hardware typically hinge on considerations of stability of the design and number of units to be produced rather than any issues involved in translating from the software domain to the hardware domain. Generally, a design that is still subject to frequent change is preferred to be implemented in software, because re-spinning a hardware implementation is more expensive than re-spinning a software design. Generally, a design that is stable and will be produced in large volume is preferred to be implemented in hardware (e.g., in an ASIC) because for large production runs the hardware implementation is less expensive than software implementations. Often a design is developed and tested in a software form and then later transformed, by design rules well-known in the art, to an equivalent hardware implementation in an ASIC that hardwires the instructions of the software. In the same manner as a machine controlled by a new ASIC is a particular machine or apparatus, likewise a computer that has been programmed and/or loaded with executable instructions is a particular machine or apparatus.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Figure 16:
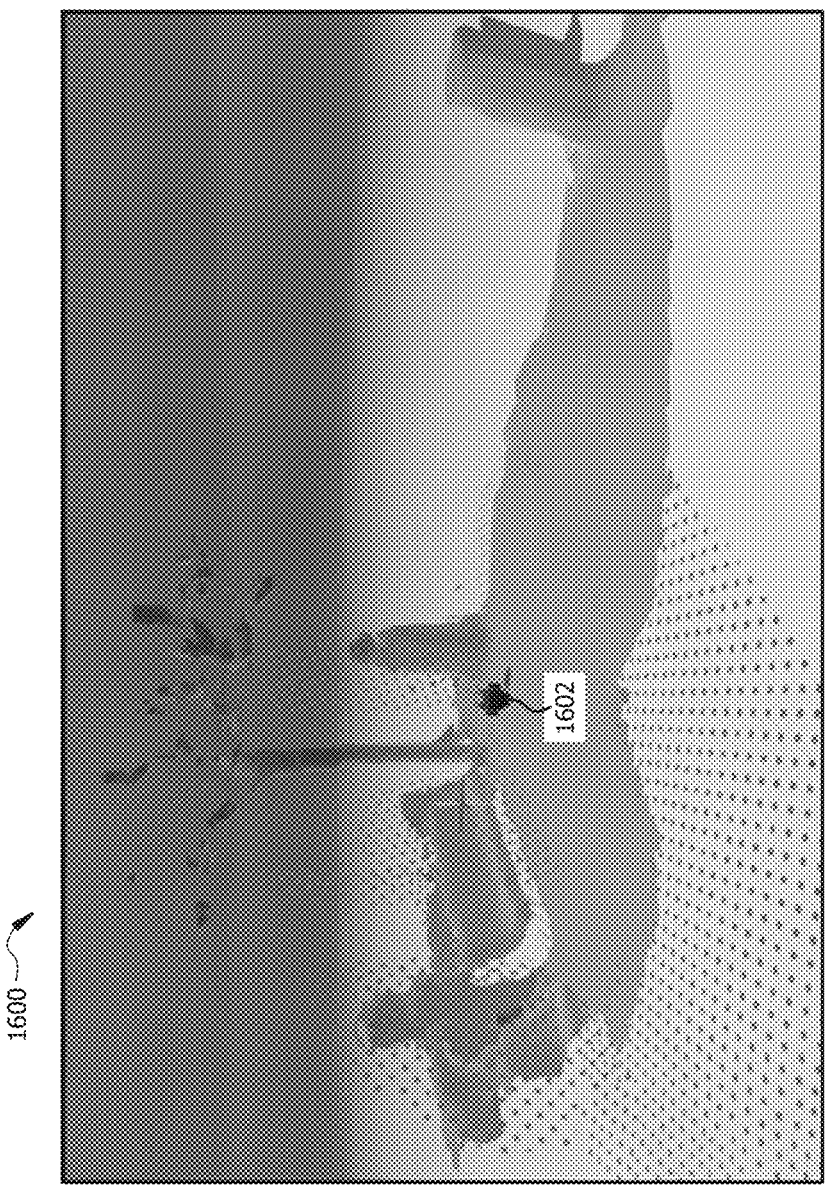
FIG. 16 is an image of an example partial spatial map in accordance with aspects of the disclosure.

Referring now to FIG. 16, an image of an example partial spatial map 1600 is shown. The partial spatial map is generated based on data provided by a SLAM capable device, as discussed below. In some examples, the SLAM capable device is the computing device 30, described above. The spatial computing device, which may be, for example, the augmentation control server 34, the local network node, or a spatial computing device 1702 as described below, receives data representative of an environment depictured by the partial spatial map 1600 and, based on that data, generates the partial spatial map 1600. In some examples, the environment bay be a context environment 200, or the spatial map may be used in part to form a context environment 200, as described above. After generating the partial spatial map 1600, the spatial computing device may localize electronic devices registered with, or communicatively couple to, the spatial computing device, in the partial spatial map 1600. In at least some examples, avatar 1602 is representative of an electronic device (e.g., computing device 30, electro-tactile stimulator 28, augmentation control server 34, etc.) that has been localized within the partial spatial map 1600. In such an example, avatar 1602 is directionally oriented based on a detected or determined orientation of the electronic device for which the avatar 1602 is representative. In other examples, avatar 1602 is representative of a digital element, such as an augmented reality element, placed on the spatial map by a user interacting with the spatial map via the spatial computing device and a device of the user. In either example, the avatar 1602 may be viewable by users viewing the spatial map in a bird's eye view and/or on a display of a user device when the user device is oriented toward an area corresponding to an area of the spatial map in which the avatar 1602 is present.

Figure 17:
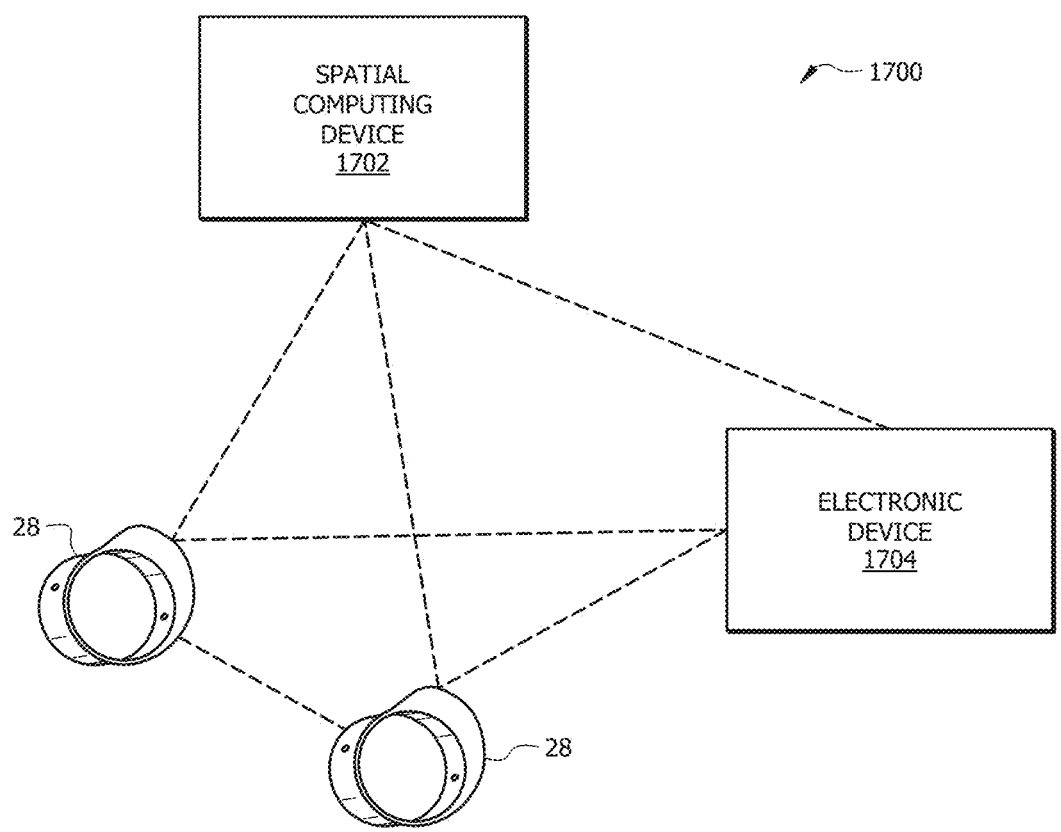
FIG. 17 is a diagram of an example computing environment in which triangulation is performed in accordance with aspects of the disclosure.

Turning now to FIG. 17, a diagram of an example computing environment 1700 in which triangulation is performed is shown. The computing environment 1700 includes two electro-tactile stimulators 28, for example, as may be worn on separate hands of a user. The computing environment 1700 may also include a spatial computing device 1702 as described herein, and an electronic device 1704. In at least some the spatial computing device 1702 may be, may be a component of, may be co-housed with, or may otherwise share at least some processing resources with the smart home hub 102, the augmentation control server 34, the local network node, etc. The electronic device 1704 may be a smart phone, a tablet computer, etc. that is in communication with the spatial computing device 1702 and the user input devices 1700. In at least some examples, the electronic device may be the computing device 30, as described above. As illustrated in FIG. 17, dashed lines are lines of wireless communication between devices. Although dashed lines are shown between devices, at a given point in time not all devices may be communicating with all other devices that they are capable of communicating with.

As discussed above, the electro-tactile stimulator 28 may have a generally ring-shaped appearance and be adapted to be worn by a user on a finger. For example, at least some implementations of the electro-tactile stimulator 28 are adapted and/or configured to be worn on a user's index finger (e.g., a finger of a hand immediately adjacent to a thumb of the hand). In further examples, the electro-tactile stimulator 28 is adapted to be used in a pair, having one user input device worn on the index finger of one hand and another user input device worn on the index finger of a second hand. Together, the two electro-tactile stimulators 28 may enable feedback to a user, such as via electrodes 43, and input from a user, such as via a touch sensitive surface (not shown) integrated into a body of the electro-tactile stimulator 28. In other examples, the electro-tactile stimulator(s) 28 may not include electrodes 43 as described elsewhere herein, and may instead include a capacitive or resistive portion for receiving inputs (e.g., such as via touch input), may include one or more vibrating or haptic elements (e.g., such as piezoelectric motors) in place of one or more of the electrodes 43, etc. Generally, the electro-tactile stimulator 28 may be said to include user interaction elements (such as in an array), which may include electrodes (including the electrodes 43), haptic elements vibration motors, etc. that provide output to a user via interaction with the user's skin.

To increase precision of localization of the electro-tactile stimulators 28 within the computing environment 1700, and therefore precision of control input, of the user electro-tactile stimulators 28, in at least some examples the spatial computing device 1702 described elsewhere herein triangulates a position of the electro-tactile stimulators 28. In at least such an example, the electro-tactile stimulators 28 may be localized in the computing environment 1700 and provide functionality without interacting with a visual device 26 via sensor 27, as described elsewhere herein. For example, the position of the electro-tactile stimulators 28 may be triangulated according to any three elements in a system in which the electro-tactile stimulators 28 and the spatial computing device 1702 are implemented. Such a system may include the spatial computing device 1702, the electro-tactile stimulators 28, other user input devices not shown (e.g., wearable devices, augmented reality or smart glasses, etc.), a user computing device (e.g., the electronic device 1704, which may be a smart phone or tablet) through which the users views and/or interacts with the spatial map, etc. By triangulating the positions of the electro-tactile stimulators 28, in at least some examples, at least six degrees of motion of the electro-tactile stimulators 28 may be monitored by the spatial computing device 1702. Triangulating the positions of the electro-tactile stimulators 28 and monitoring six degrees of motion of the electro-tactile stimulators 28, in at least some examples, enables a greater range of inputs (e.g. greater sensitivity between motions and therefore a greater number of distinguishable motions or actions) to be provided by the electro-tactile stimulators 28 to a greater degree of precision than if the position of the electro-tactile stimulators 28 were not triangulated. In at least some examples, the position of an electro-tactile stimulator 28 may be determined according to two components (including the electro-tactile stimulator 28) in the computing environment 1700 rather than via triangulation, such as through analysis of a signal being transmitted between the electro-tactile stimulator 28 and one other device, such as the spatial computing device 1702 or the electronic device 1704.s In at least some examples, the spatial computing device 1702 communicates with any two of the electro-tactile stimulators 28 and/or the electronic device 1704 to triangulate a position of one, or both, of the electro-tactile stimulators 28. Alternatively, in some examples the electronic device 1704 communicates with each of the electro-tactile stimulators 28 to triangulate a position of one, or both, of the electro-tactile stimulators 28 and conveys that position information to the spatial computing device 1702. The triangulation may be performed according to any suitable means for triangulation, the scope of which is not limited herein. Based on this triangulation, movement of an electro-tactile stimulator 28 located according to triangulation may be tracked according to any of the six degrees of freedom (e.g., translation in x, y, and/or z axes and rotation about the x, y, and/or z axes).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other intervening devices and/or connections. Unless otherwise stated, "about," "approximately," or "substantially" preceding a value means +/−10 percent of the stated value or reference.

What is claimed is:

1. A sensory augmentation system, comprising:
a first electro-tactile stimulator, wherein the first electro-tactile stimulator comprises a ring having a continuous and unchangeable annular structure for wear on a finger of a user, wherein a diameter of the annular structure is determined based on a diameter of the finger, the first electro-tactile stimulator comprising:
an array of user interaction elements disposed linearly and equidistantly around an interior surface of the ring and driven by a driver and contactable to a human body to provide stimulation having a first stimulation waveform; and
a signal generation and sensing processor configured to receive data corresponding to information to be communicated to the user,
wherein the signal generation and sensing processor generates a first instruction to the driver, the first instruction corresponding to the first stimulation waveform, and
wherein the driver generates the stimulation having the first stimulation waveform in response to the first instruction.

2. The sensory augmentation system according to claim 1, comprising a second electro-tactile stimulator, wherein the first and second electro-tactile stimulators are wearable on different fingers and localized in the sensory augmentation system according to triangulation.

3. The sensory augmentation system according to claim 1, wherein the driver drives a first user interaction element of the array of user interaction elements with the electrical stimulation having the first stimulation waveform and drives a second user interaction element of the array of user interaction elements with the electrical stimulation having a second stimulation waveform different from the first stimulation waveform.

4. The sensory augmentation system according to claim 3, wherein each waveform corresponds to a physical sensation representing a different alphabet character.

5. The sensory augmentation system according to claim 3, wherein each waveform corresponds to a different alphabet character, and wherein the first instruction comprises data representing text.

6. The sensory augmentation system according to claim 5, further comprising glasses having a built-in image projector configured to project an image corresponding to the text.

7. The sensory augmentation system according to claim 1, wherein the signal generation and sensing processor is in electronic communication with a smartphone and receives data therefrom corresponding to text to communicate to a user via the first stimulation waveform.

8. A method of sensory augmentation, comprising:
providing, by a computing device, a wireless transmission corresponding to text;
receiving, by a first electro-tactile stimulator, the wireless transmission, wherein the first electro-tactile stimulator comprises a ring having a continuous and unchangeable annular structure for wear on a finger of a user, wherein a diameter of the annular structure is determined based on a diameter of the finger;
generating, by a signal generation and sensing processor of the first electro-tactile stimulator, a first instruction to an electrode driver, the first instruction corresponding to a first stimulation waveform representing the text;
generating, by the electrode driver, the first stimulation waveform in response to the first instruction; and
providing, by an electrode array disposed linearly and equidistantly around on an interior surface of the ring and driven by the electrode driver, electrical stimulation to a human body, the electrical stimulation corresponding to the text.

9. The method of sensory augmentation according to claim 8, further comprising providing a second electro-tactile stimulator, wherein the first and second electro-tactile stimulators are wearable on different fingers.

10. The method of sensory augmentation according to claim 8, wherein the electrode driver drives a first electrode of the array of electrodes with the electrical stimulation having the first stimulation waveform and drives a second electrode of the array of electrodes with the electrical stimulation having a second stimulation waveform different from the first stimulation waveform.

11. The method of sensory augmentation according to claim 10, wherein each waveform corresponds to a physical sensation representing a different alphabet character.

12. The method of sensory augmentation according to claim 10, wherein each waveform corresponds to a different alphabet character and wherein the first instruction comprises data representing text.

13. The method of sensory augmentation according to claim 8, wherein the computing device is a smartphone and the wireless transmission corresponds to text to communicate to a user via the first stimulation waveform.

14. The method of sensory augmentation according to claim 13, further comprising projecting, by glasses having a built-in image projector, an image corresponding to the text.

15. A sensory augmentation system, comprising:
an annular electro-tactile stimulator having an unchangeable diameter determined based on a diameter of a finger of a user, the electro-tactile stimulator for wear on the finger of the user and comprising:
an array of user interaction elements disposed linearly and equidistantly around an exterior annular surface of the electro-tactile stimulator so as to contact the finger of the user to provide stimulation having a stimulation waveform; and
a processor configured to:
receive data corresponding to information to be communicated to the user; and
cause a first user interaction element of the array of user interaction elements to provide the stimulation waveform to the finger of the user responsive to the received data.

16. The system of claim 15, further comprising a driver in communication with the processor and the first user interaction element of the array of user interaction elements, wherein the processor generates an instruction responsive to receiving the data and provides the instruction to the driver.

17. The system of claim 16, wherein the driver generates a stimulation having the stimulation waveform in response to the instruction and provides the stimulation to the first user interaction element.

18. The system of claim 15, wherein the array of user interaction elements is disposed along an equator of the annular surface.

* * * * *